US008748372B2

(12) United States Patent
Luban et al.

(10) Patent No.: US 8,748,372 B2
(45) Date of Patent: Jun. 10, 2014

(54) POLYNUCLEOTIDE ENCODING A TRIM-CYP POLYPEPTIDE, COMPOSITIONS THEREOF, AND METHODS OF USING SAME

(75) Inventors: Jeremy Luban, New York, NY (US); David Sayah, San Francisco, CA (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 13/331,363

(22) Filed: Dec. 20, 2011

(65) Prior Publication Data

US 2013/0084327 A1 Apr. 4, 2013

Related U.S. Application Data

(60) Division of application No. 11/650,384, filed on Jan. 5, 2007, now Pat. No. 8,084,593, which is a continuation of application No. PCT/US2005/023803, filed on Jul. 6, 2005.

(60) Provisional application No. 60/585,925, filed on Jul. 6, 2004.

(51) Int. Cl.
*C07K 19/00* (2006.01)
*C12N 5/07* (2010.01)
*A61P 31/18* (2006.01)
*A61K 9/127* (2006.01)

(52) U.S. Cl.
USPC ............ 514/3.8; 530/350; 424/450; 435/325

(58) Field of Classification Search
None
See application file for complete search history.

(56) References Cited

U.S. PATENT DOCUMENTS 5,399,346 A   3/1995   Anderson et al.

FOREIGN PATENT DOCUMENTS

EP          336523        10/1989
WO      WO-90/11092     10/1990

OTHER PUBLICATIONS

Berthoux et al., "As2O3 enhances retroviral reverse transcription and counteracts Ref1 antiviral activity," J. Virol. 77:3167-3180 (2003).
Berthoux et al., "Lv1 inhibition of human immunodeficiency virus type 1 is counteracted by factors that stimulate synthesis or nuclear translocation of viral cDNA" J. Virol. 78: 11739-11750 (2004).
Besnier, C., Takeuchi, Y. & Towers, G. Restriction of lentivirus in monkeys. Proc. Natl Acad. Sci. USA 99, 11920-11925 (2002).
Bieniasz, P. D., "Restriction factors: a defense against retroviral infection," Trends Microbiol. 11:286-291 (2003).
Bowerman et al., "A nucleoprotein complex mediates the integration of retroviral DNA," Genes Dev 3:469-478 (1989).
Braaten et al., "Cyclosporine A-resistant human immunodeficiency virus type 1 mutants demonstrate that Gag encodes the functional target of cyclophili," A. J. Virol. 70:5170-5176 (1996).
Braaten, D. & Luban, J. Cyclophilin A regulates HIV-1 infectivity, as demonstrated by gene targeting in human T cells. EMBO J. 20, 1300-1309 (2001).
Brigham et al., "Rapid Communication: In vivo Transfection of Murine Lungs with a Functioning Prokaryotic Gene Using a Liposome Vehicle," Am J. Med. Sci 298:278-281 (1989).
Canonico et al., "Expression of a CMV promoter driven Human α-1 antitrypsin gene in cultured lung endothelial cells and in the lungs of rabbits," Clin Res 39:219A (1991).
Colgan et al., "Binding of the human immunodeficiency virus type 1 Gag polyprotein to cyclophilin A is mediated by the central region of capsid and requires Gag dimerization," J. Virol. 70:4299-4310 (1996).
Cowan, S. et al. Cellular inhibitors with Fv1-like activity restrict human and simian immunodeficiency virus tropism. Proc. Natl Acad. Sci. USA 99, 11914-11919 (2002).
Damert et al., "Leptin receptor isoform 219.1: an example of protein evolution by LINE-1-mediated human-specific retrotransposition of a coding SVA element," Mol. Biol. Evol. 21, 647-651 (2004).
Dewannieux et al., "LINE-mediated retrotransposition of marked Alu sequences," Nature Genet. 35, 41-48 (2003).
Ejima et al., "Trans mobilization of genomic DNA as a mechanism for retrotransposon-mediated exon shuffling," Hum. Mol. Genet. 12, 1321-1328 (2003).
Esnault et al., "Human LINE retrotransposons generate processed pseudogenes," Nature Genet. 24, 363-367 (2000).
Fassati et al., "Characterization of intracellular reverse transcription complexes of Moloney murine leukemia virus," J Virol 73:8919-8925 (1999).
Fehr et al., "A, B, C and D, novel cyclophilin-binding compounds isolated from *Streptomyces* sp. A92-308110. II. Structure elucidation, stereochemistry and physico-chemical properties," J. Antibiot. (Tokyo) 52, 474-479 (1999).
Feng et al., "Human L1 retrotransposon encodes a conserved endonuclease required for retrotransposition," Cell 87, 905-916 (1996).
Franke, E. K., Yuan, H. E. & Luban, J. "Specific incorporation of cyclophilin A into HIV-1 virions," Nature 372, 359-362 (1994).
Freemont, P. S., "RING for destruction?," Curr. Biol. 10:R84-R87 (2000).
Gilbert, W., "Why genes in pieces?," Nature 271, 501 (1978).
Gyuris et al., "Cdi1, a human G1 and S phase protein phosphatase that associates with Cdk2," Cell 75:791-803 (1993).

(Continued)

*Primary Examiner* — Louise Humphrey
(74) *Attorney, Agent, or Firm* — Wilmer Cutler Pickering Hale and Dorr LLP

(57) ABSTRACT

The invention provides an isolated nucleic acid encoding a TRIM-cyclophilin A fusion sequence encoding a TRIMcyp fusion protein which is active as an anti-viral agent, and in particular an anti-HIV-1 agent. The invention provides for a nucleic acid encoding a polypeptide having both TRIM activity and cyclophilin activity. The invention provides for an isolated polynucleotide encoding a TRIM-cyclophilin fusion protein, or variants thereof retaining the TRIM and cyclophilin activities. The invention provides for compositions thereof, antibodies that specifically bind thereto, and vectors and host cells comprising the nucleic acid or polypeptide. In addition, the invention provides for methods for treating or preventing viral infection, or reducing viral load in a subject comprising administering the nucleic acid, polypeptide, vector, or composition to the subject in an amount effective to treat or prevent the viral infection.

10 Claims, 13 Drawing Sheets

(56) References Cited

OTHER PUBLICATIONS

Hatziioannou et al., "Retrovirus resistance factors Ref1 and Lv1 are species-specific variants of TRIM5_," Proc. Natl. Acad. Sci. USA 101:10774-10779 (2004).

Hazinski et al., "Localization and induced Expression of Fusion Genes in the Rat Lung," Am. J. Resp. Cell Mol. Biol. 4:206-209 (1991).

Hofmann, W. et al. Species-specific, postentry barriers to primate immunodeficiency virus infection. J. Virol. 73, 10020-10028 (1999).

International Search report and Written Opinion mailed on Apr. 29, 2008 for International Application No. PCT/US05/23803 filed Jul. 6, 2005.

Jackson, A. L. et al., "Expression profiling reveals off-target gene regulation by RNAi," Nature Biotechnol. 21, 635-637 (2003).

Kazazian, H. H. Jr.,"Mobile elements: drivers of genome evolution," Science 303, 1626-1632 (2004).

Keckesova et al., "The human and African green monkey TRIM5α genes encode Ref1 and Lv1 retroviral restriction factor activities," Proc. Natl. Acad. Sci. USA 101:10780-10785 (2004).

Lee et al., "In defense of the cell: TRIM5α interception of mammalian retroviruses," Proc. Natl. Acad. Sci. USA 101: 10496-10497 (2004).

Long et al., "Natural selection and the origin of jingwei, a chimeric processed functional gene in *Drosophila*," Science 260, 91-95 (1993).

Luban et al., "Human immunodeficiency virus type 1 Gag protein binds to cyclophilins A and B," Cell 73, 1067-1078 (1993).

McClintock, B., "The origin and behavior of mutable loci in maize," Proc. Natl Acad. Sci. USA 36, 344-355 (1950).

Moran et al., "Exon shuffling by L1 retrotransposition," Science 283, 1530-1534 (1999).

Nabel et al., "Site-Specific Gene Expression in vivo by Direct Gene Transfer into the Arterial Wall," Science 249:1285-1288 (1990).

Nisole et al., "A Trim5-cyclophilin A fusion protein found in owl monkey kidney cells can restrict HIV-1," Proc. Natl. Acad. Sci. USA 101:13324-13328 (2004).

Perron et al., "TRIM5α mediates the postentry block to N-tropic murine leukemia viruses in human cells," Proc. Natl. Acad. Sci. USA 101:11827-11832 (2004).

Ponting et al., "SPRY domains in ryanodine receptors (Ca(2+)-release channels)," Trends Biochem Sci 22:193-194 (1997).

Reymond, A. et al., "The tripartite motif family identifies cell compartments," EMBO J. 20, 2140-2151 (2001).

Roy-Engel, A. M. et al.,"Non-traditional Alu evolution and primate genomic diversity," J. Mol. Biol. 316, 1033-1040 (2002).

Saphire et al., "Host cyclophilin A mediates HIV-1 attachment to target via heparans," EMBO J, vol. 18,pp. 6771-6785 (1999).

Sawyer et al., "Positive selection of primate TRIM5alpha identifies a critical species-specific retroviral restriction domain," Proc Natl Acad Sci U S A 102:2832-2837 (2005).

Sayah et al., "Cyclophilin A retrotransposition into TRIM5 explains Owl Monkey resistance to HIV-1," Nature, 430, pp. 569-573 (Jul. 29, 2004).

Schwartz et al., "Antiviral activity of the proteasome on incoming human immunodeficiency virus type 1," J. Virol. 72, 3845-3850 (1998).

Song et al., "Retrovirus restriction by TRIM5alpha variants from old world and new world primates," *J Virol* 79:3930-3937 (2005).

Stern et al., "Five SWI genes are required for expression of the HO gene in yeast," J. Mol. Biol. 178:853-868 (1984).

Stoye, J. P. "An intracellular block to primate lentivirus replication," Proc. Natl. Acad. Sci. USA 99:11549-11551 (2002).

Stremlau et al., "Species-Specific Variation in the B30.2(SPRY) Domain of TRIM5α Determines the Potency of Human Immunodeficiency Virus Restriction," *J Virol* 79:3139-3145 (2005).

Stremlau, M. et al. "The cytoplasmic body component TRIM5a restricts HIV-1 infection in Old World monkeys.," Nature 427, 848-853 (2004).

Thali, M. et al. "Functional association of cyclophilin A with HIV-1 virions," Nature 372, 363-365 (1994).

Towers et al., "A conserved mechanism of retrovirus restriction in mammals," Proc. Natl. Acad. Sci. USA 97:12295-12299 (2000).

Towers et al., "Abrogation of Ref1 retrovirus restriction in human cells," J Virol 76:2548-2550 (2002).

Towers, G. J. et al., "Cyclophilin A modulates the sensitivity of HIV-1 to host restriction factors," Nature Med. 9, 1138-1143 (2003).

Wei, W. et al., "Human L1 retrotransposition: cis preference versus trans complementation," Mol. Cell. Biol. 21, 1429-1439 (2001).

Welker et al,"Biochemical and structural analysis of isolated mature cores of human immunodeficiency virus type 1," J Virol 74:1168-1177 (2000).

Wolff et al., "Direct Gene Transfer into Mouse Muscle in vivo," Science 247:1465-1468 (1990).

Wu et al., "Nup358, a cytoplasmically exposed nucleoporin with peptide repeats, Ran-GTP binding sites, zinc fingers, a cyclophilin A homologous domain, and a leucine-rich region," J. Biol. Chem. 270, 14209-14213 (1995).

Xu, L. et al., "BTBD1 and BTBD2 colocalize to cytoplasmic bodies with the RBCC/tripartite motif protein, TRIM5d," Exp. Cell Res. 288, 84-93 (2003).

Yap et al., "A single amino acid change in the SPRY domain of human Trim5alpha leads to HIV-1 restriction," Curr Biol 15:73-78 (2005).

Yap et al., "TRIM5α protein restricts both HIV-1 and murine leukemia virus," Proc. Natl. Acad. Sci. USA 101:10786-10791 (2004).

Zennou et al., "HIV-1 genome nuclear import is mediated by a central DNA flap," Cell 101:173-185 (2000).

Zhang et al., "Millions of years of evolution preserved: a comprehensive catalog of the processed pseudogenes in the human genome," Genome Res. 13, 2541-2558 (2003).

Nakayama EE, et al., "A specific region of 37 amino acid residues in the SPRY (B30.2) domain of African green monkey TRIM5alpha determines species-specific restriction of simian immunodeficiency virus SIVmac infection", J. Virol., Jul. 2005, vol. 79, No. 14, pp. 8870-8877.

Luo, Z., et al., "Roles in cell-to-cell fusion of two conserved hydrophobic regions in murine coronavirus spike protein", Virology, vol. 244, pp. 483-494, May 1998.

Figures 2a-2f a

```
                    ————————————————Ring Finger————————————————
MASRILVNIKEEVTCPICLELLTEPLSLDCGHSFCQACITANHKKSMPHQGERSCPLCRI
                                                ————B Box 2————
SYSSENLRPNRHLVNIVERLREVMLSPEEGQKVDHCAHHGEKLVLPCQQDGNVICWLCER
————————————————————————————Coiled-Coil————————————————————
SQEHRGHQTFLVEEVAQKYREKLQVALEMMRQKQKDAEKLEADVREEQASWKIQIQNDKT
——————————————————————————————————————
NIMAEFKKRRDILDCEESKELQNLEKEEKNILKRLVQSENDMVLQTQSVRVLISDLEHRL
QGSVMELLQGVDGVIKRIEKVTLQNPKTFLNEKRRIFQTPDLKGTLQVFKEPTEVQRYWD
AAAWDLVASAMVNPTVFFDIAVDGEPLGRVSFELFADKVPKTAENFRALSTGEKGFGYKG
SCFHRIIPGFMCQGGDFTRHNGTGGKSIYGEKFDDENFILKHTGPGILSMANAGPNTNGS
QFFICTAKTEWLDGKHVVFGKVKEGMNVVEAMERFGCRYGKTSKKITIADCGQL*
```

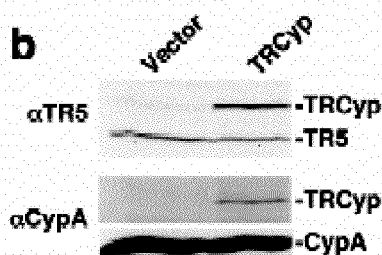

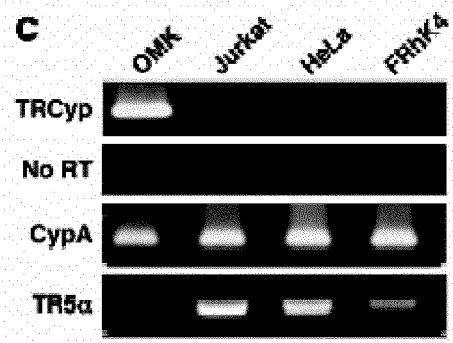

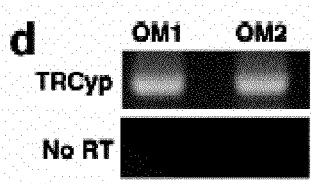

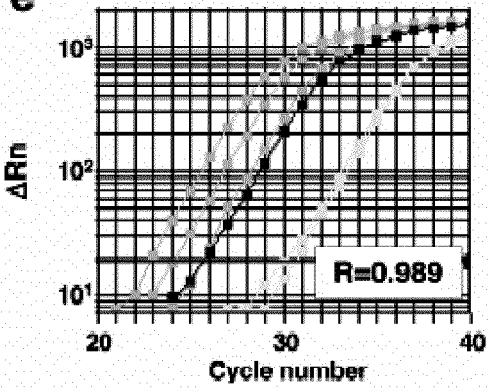

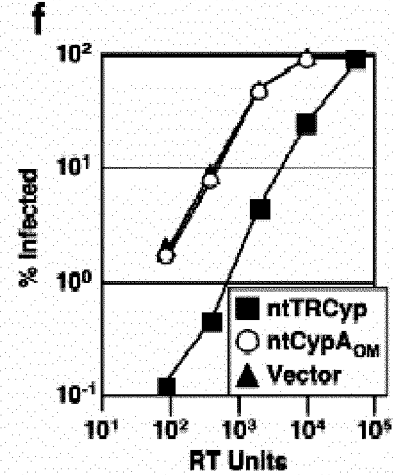

Figures 4a-4c

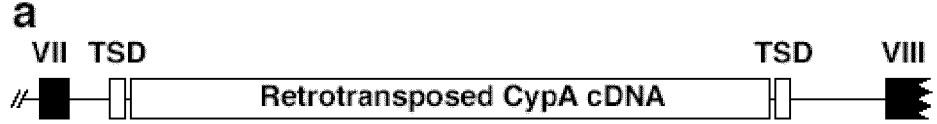

a
VII TSD                                              TSD     VIII
//■——□——[ Retrotransposed CypA cDNA ]——□——■▰ b
```
                ————————exon 7————————
At   AGCCGACAGAAGTCCAACGCTACTGGGgtaaggagaaatcacattattat
Hs   ...T......T....G.....................g.........c..
                                              TSD
At   aagccacccagtatgattatctttatcttttaagaattttatgttctggc
Hs   .........t.cggc-.....a....ta..----.tc.....c..t.---

————Retrotransposed CypA cDNA————
At   tttgcagACGCCGCCGCCTGGGACCTTGTAGCATCAGCCATG——▶
Hs   --------------------------------------------
``` c
```
      ———Retrotransposed CypA cDNA———        TSD
At   AATAAAGACTAAATAACAAAAAAAAAAAAAAAaagaattttatgttctct
Hs   --------------------------------------------.....

At   attaggtctcatgttttaagatttatatttcttcttccagcacacacata
Hs   ......-....................ga....c......ag........

At   acctaccttccttataacttctgaacaaggttccttccagttttctttc
Hs   ..t.....c...............a............c.........c..

At   aaggctttattaagatttctctcatat------aatgtta------tcc
Hs   ...t......c...............cacaaa..a....cattata...
                                              ————exon 8————
At   cttacctgacctgttaattttttacagCTCATGTGACACTGGT——▶
Hs   ....g...................c.....T.G........G...C
```

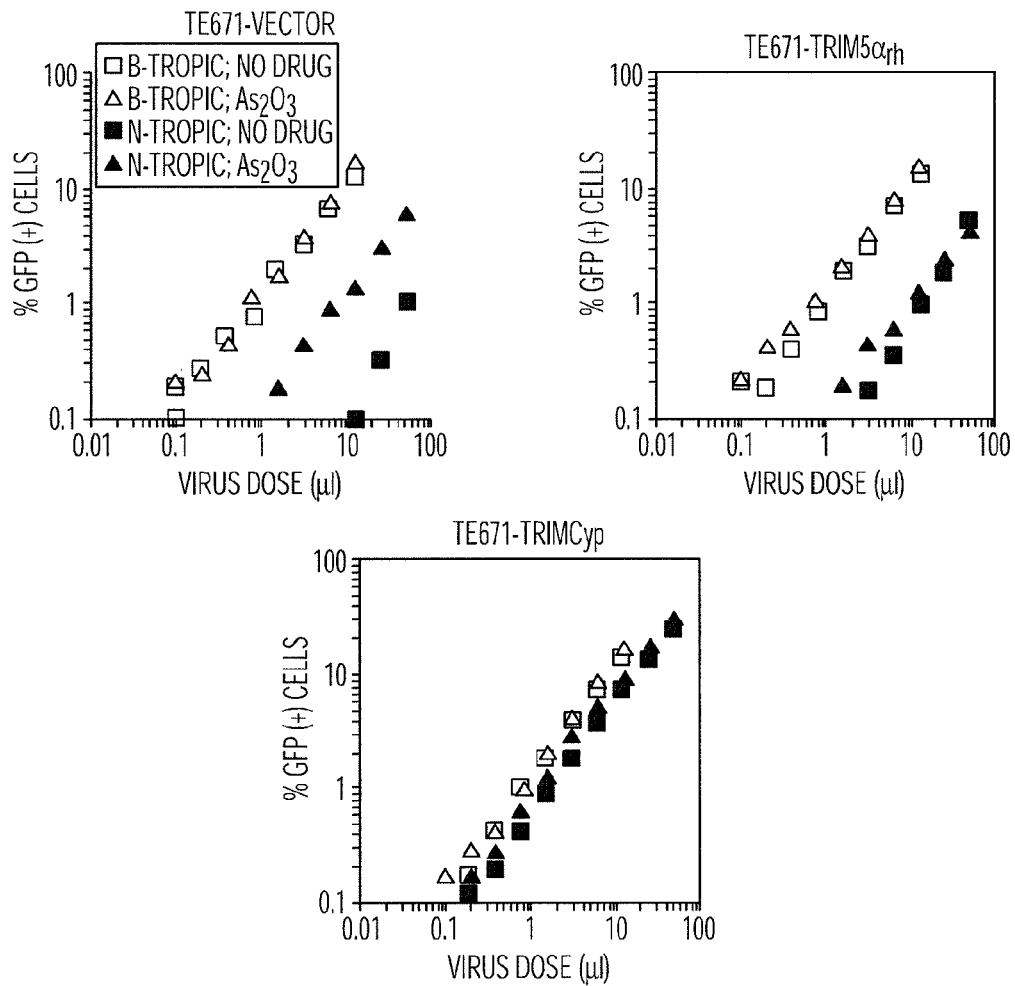
FIG. 7A
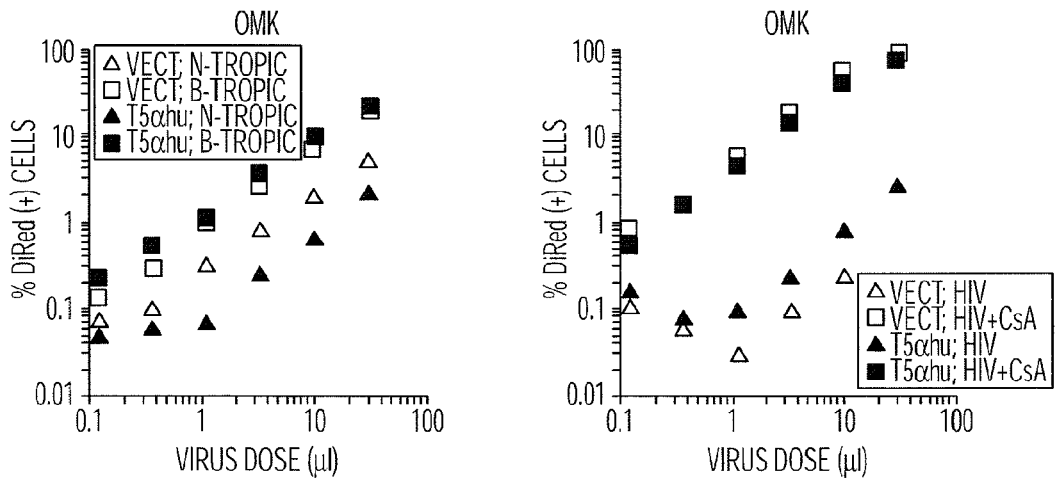
FIG. 7B
FIG. 7C

SEQUENCE LISTING

<160> NUMBER OF SEQ ID NOS: 37

<210> SEQ ID NO 1
<211> LENGTH: 1811
<212> TYPE: DNA
<213> ORGANISM: Aotus trivirgatus

<400> SEQUENCE: 1

| | | |
|---|---|---|
| tgcaggcccc tggattgaga atataaacaa caattcttat tatccctttt actggtttgc | 60 |
| acggggagag agaagccaaa gacctgactg ggatctgtga gcaagaggag cctcagcagc | 120 |
| caggacaggc aagagtagtg gagcagctac tatggcttcc agaatcctgg tcaatataaa | 180 |
| ggaggaggtg acctgcccca tctgcctgga actcctgaca gaaccctga gcctggactg | 240 |
| tggccatagc ttctgccaag catgcatcac tgcaaatcac aaaaagtcta tgccacacca | 300 |
| aggagagaga agctgccctt tgtgccggat cagttactcg tctgagaacc tgcggcctaa | 360 |
| tcggcatttg gtcaacatag tggagaggct cagggaggtc atgctgagcc cagaggaggg | 420 |
| gcagaaggtt gatcactgtg cacaccatgg agagaaactt gtactcttct gtcagcagga | 480 |
| tggaaatgtc atttgctggc tttgtgagcg gtctcaagaa caccgtgggc accagacatt | 540 |
| ccttgtggag gaggttgcac agaaataccg agaaaagctc caggtagctc tggagatgat | 600 |
| gaggcagaag cagaaggatg ctgaaaagtt ggaagctgac gtcagagaag agcaagcttc | 660 |
| ctggaagatt caaatacaaa atgacaaaac caacatcatg gcagagttta aaaaacggag | 720 |
| agacatcctg gactgtgagg agagcaaaga gttgcaaaac ctggagaagg aggagaaaaa | 780 |
| cattctgaaa agacttgtac agtctgaaaa tgacatggtg ctgcagaccc agtccgtgag | 840 |
| agtgctcatc tcagatctgg agcatcgcct gcagggtca gtgatggagc tgttacaggg | 900 |
| tgtggatggt gtcataaaaa ggattgagaa agtgactttg cagaatccaa aaaccttct | 960 |
| taatgaaaaa aggagaatat ttcaaactcc tgatctgaaa ggaacactac aagtgtttaa | 1020 |
| agagccgaca gaagtccaac gctactggga cgccgccgcc tgggaccttg tagcatcagc | 1080 |
| catggtcaat cctactgtgt tcttcgacat tgccgtcgat ggcgagccct gggccgcgt | 1140 |
| ctccttcgag ctgtttgcag acaaggttcc aaagacagca gaaaactttc gtgctctgag | 1200 |
| cactggagag aaaggatttg gttataaggg ttcctgcttt cacagaatta ttccagggtt | 1260 |
| tatgtgtcag ggtggtgact tcacacgcca taatggcact ggtggcaagt ccatctacgg | 1320 |
| ggagaaattt gatgatgaga acttcatcct aaagcataca ggtcccggta tcttgtccat | 1380 |
| ggcaaatgct ggacccaaca caaacggttc ccagtttttc atctgcactg ccaagactga | 1440 |
| gtggttggat ggcaagcatg tggtctttgg caaggtgaaa gaaggcatga atgttgtgga | 1500 |
| ggccatggag cgctttgggt gcaggtatgg caagaccagc aaaagatca ccattgctga | 1560 |
| ctgtggacaa ctttaataag tttgacttgt gttttgtctt caccaccaga ccattccttc | 1620 |
| tgtagctcag gagagcaccc ctccacccca tttgctcgca gtatcctaca atctgtgctc | 1680 |
| tcgctgcagt tccctttggg ttccatgttt tccttgttcc cttccatgcc tagctggatt | 1740 |
| gcagagttga gttaagttt atgattatga aataaagact aaataacaaa aaaaaaaaa | 1800 |
| aaaaaaaaa a | 1811 |

<210> SEQ ID NO 2
<211> LENGTH: 2059
<212> TYPE: DNA
<213> ORGANISM: Aotus trivirgatus

<400> SEQUENCE: 2

```
tttcttaatg aaaaaggaga atatttcaaa ctcctgatct gaaaggaaca ctacaagtgt      60
ttaaaggtga ggagagctgg atcaactgcg gggttgtgga atgcaagtcc cgactgtgtc     120
agggtgctaa atgagaaaaa gagtgtggtt tccaaatatg atagaggggg atggggaaga     180
tggatattat ctgctgctga tgggattata tttaatgaga aatggctagg tggctgtttc     240
accctgtcat tcaccagttt actgccctac catagggcat gcctactctt tccctaatct     300
ggagagaaaa tgaatttcag tgctgactcc ttttacttgt atccaatatt atgcattttt     360
atcatttcag agccgacaga agtccaacgc tactggggta aggagaaatc acattattat     420
aagccaccca gtatgattat ctttatcttt aagaatttt atgttctggc tttgcagacg     480
ccgccgcctg ggaccttgta gcatcagcca tggtcaatcc tactgtgttc ttcgacattg     540
ccgtcgatgg cgagcccttg ggccgcgtct ccttcgagct gtttgcagac aaggttccaa     600
agacagcaga aaactttcgt gctctgagca ctggagagaa aggatttggt tataagggtt     660
cctgctttca cagaattatt ccagggttta tgtgtcaggg tggtgacttc acacgccata     720
atggcactgg tggcaagtcc atctacgggg agaaatttga tgatgagaac ttcatcctaa     780
agcatacagg tcccggtatc ttgtccatgg caaatgctgg acccaacaca aacggttccc     840
agttttcat ctgcactgcc aagactgagt ggttggatgg caagcatgtg gtctttggca     900
aggtgaaaga aggcatgaat gttgtggagg ccatggagcg ctttgggtgc aggtatggca     960
agaccagcaa aaagatcacc attgctgact gtggacaact ttaataagtt tgacttgtgt    1020
tttgtcttca ccaccagacc attccttctg tagctcagga gagcacccct ccaccccatt    1080
tgctcgcagt atcctacaat ctgtgctctc gctgcagttc cctttgggtt ccatgttttc    1140
cttgttccct tccatgccta gctggattgc agagttgagt taagtttatg attatgaaat    1200
aaagactaaa taacaaaaaa aaaaaaaaaa agaattttat gttctctatt aggtctcatg    1260
ttttaagatt tatatttctt cttccagcac acacataacc taccttcct tataacttct     1320
gaacaaggtt ccttccagtt ttcttttcaag gctttattaa gatttctctc atataatgtt    1380
atcccttacc tgacctgtta attttttac agctcatgtg acactggttc caagtcaccc     1440
ttcatgtact gtcatttctg aagatgagag acaagtgaga tatcagaaac ggatatatca    1500
accatttctg aaagtcaagt atttttgtgg cgtcctgggc tccccaagta tcacatcagg    1560
gaaacattac tgggaggtag acgtgtccaa taaaagtgag tggatcctgg gggtatgtgt    1620
tagcttgaag cgcactgcaa gttgtagtgt tccaagaatt gaaaatgatc aacctaaaaa    1680
tggctactgg gttataggt tacggaatgc agataactat agtgctttcc aggatgcagt     1740
tgaatatagt gatttccagg atggttcccg ctctactcct tctgctcctt tgatcgtgcc    1800
cctctttatg actatttgtc ctaatcgtgt tggagttttc ctagactatg aggcttgcac    1860
tgtctcattc ttcaatgtca caaacaatgg atttctcatc tataagtttt ctaactgtca    1920
tttttgttat cctgtatttc catatttcag tcctatgaca tgtgaattac ccatgactct    1980
gtgctcacca agctcttgaa ctatcttaaa tactcagccg cttcttaccc aggtgcatct    2040
catacacctg aaccttcat                                                  2059
```

<210> SEQ ID NO 3
<211> LENGTH: 737
<212> TYPE: DNA
<213> ORGANISM: Aotus trivirgatus

<400> SEQUENCE: 3

```
ccttgtagca tcagccatgg tcaatcctac cgtgttcttc gacattgccg tcgatggcga    60
gcccttgggc cgcgtctcct tcgagctgtt tgcagacaag gttccaaaga cagcagaaaa   120
ctttcgtgct ctgagcactg gagagaaagg atttggttat aagggttcct gctttcacag   180
aattattcca gggtttatgt gtcagggtgg tgacttcaca cgccataatg gcactggtgg   240
caagtccatc tacggggaga aatttgatga cgagaacttc atcctaaagc atacaggtcc   300
cggtatcttg tccatggcaa atgctggacc caacacaaac ggttcccagt ttttcatctg   360
cactgtcaag actgagtggt tggatggcaa gcatgtggtc tttggcaagg tgaaagaagg   420
catgaatatt gtggaggcca tggagcgctt tgggtccagg aatggcaaga ccagcaagaa   480
gatcaccatt gctgactgtg acaacttta  ataagtttga cttgtgtttt gtcttcacca   540
ccagaccatt cctttcgtag ctcaggagag caccccctcca ccccatttgc tcgcagtatc   600
ctaaaatctg tgctctcgct gcagttccct ttgggtccca tgttttcctt gttcccttcc   660
atgcctagct ggattgcaga gttgagttaa gtttatgatt atgaaataaa gactaaataa   720
caaaaaaaaa aaaaaaa                                                  737

<210> SEQ ID NO 4
<211> LENGTH: 474
<212> TYPE: PRT
<213> ORGANISM: Aotus trivirgatus

<400> SEQUENCE: 4

Met Ala Ser Arg Ile Leu Val Asn Ile Lys Glu Glu Val Thr Cys Pro
 1               5                  10                  15

Ile Cys Leu Glu Leu Leu Thr Glu Pro Leu Ser Leu Asp Cys Gly His
                20                  25                  30

Ser Phe Cys Gln Ala Cys Ile Thr Ala Asn His Lys Lys Ser Met Pro
            35                  40                  45

His Gln Gly Glu Arg Ser Cys Pro Leu Cys Arg Ile Ser Tyr Ser Ser
        50                  55                  60

Glu Asn Leu Arg Pro Asn Arg His Leu Val Asn Ile Val Glu Arg Leu
 65                  70                  75                  80

Arg Glu Val Met Leu Ser Pro Glu Glu Gly Gln Lys Val Asp His Cys
                85                  90                  95

Ala His His Gly Glu Lys Leu Val Leu Phe Cys Gln Gln Asp Gly Asn
            100                 105                 110

Val Ile Cys Trp Leu Cys Glu Arg Ser Gln Glu His Arg Gly His Gln
        115                 120                 125

Thr Phe Leu Val Glu Glu Val Ala Gln Lys Tyr Arg Glu Lys Leu Gln
    130                 135                 140

Val Ala Leu Glu Met Met Arg Gln Lys Gln Lys Asp Ala Glu Lys Leu
145                 150                 155                 160

Glu Ala Asp Val Arg Glu Glu Gln Ala Ser Trp Lys Ile Gln Ile Gln
                165                 170                 175

Asn Asp Lys Thr Asn Ile Met Ala Glu Phe Lys Lys Arg Arg Asp Ile
            180                 185                 190

Leu Asp Cys Glu Glu Ser Lys Glu Leu Gln Asn Leu Glu Lys Glu Glu
        195                 200                 205

Lys Asn Ile Leu Lys Arg Leu Val Gln Ser Glu Asn Asp Met Val Leu
    210                 215                 220

Gln Thr Gln Ser Val Arg Val Leu Ile Ser Asp Leu Glu His Arg Leu
225                 230                 235                 240

Gln Gly Ser Val Met Glu Leu Leu Gln Gly Val Asp Gly Val Ile Lys
```

```
                    245                 250                 255
Arg Ile Glu Lys Val Thr Leu Gln Asn Pro Lys Thr Phe Leu Asn Glu
                260                 265                 270

Lys Arg Arg Ile Phe Gln Thr Pro Asp Leu Lys Gly Thr Leu Gln Val
            275                 280                 285

Phe Lys Glu Pro Thr Glu Val Gln Arg Tyr Trp Asp Ala Ala Trp
        290                 295                 300

Asp Leu Val Ala Ser Ala Met Val Asn Pro Thr Val Phe Phe Asp Ile
305                 310                 315                 320

Ala Val Asp Gly Glu Pro Leu Gly Arg Val Ser Phe Glu Leu Phe Ala
                325                 330                 335

Asp Lys Val Pro Lys Thr Ala Glu Asn Phe Arg Ala Leu Ser Thr Gly
            340                 345                 350

Glu Lys Gly Phe Gly Tyr Lys Gly Ser Cys Phe His Arg Ile Ile Pro
        355                 360                 365

Gly Phe Met Cys Gln Gly Gly Asp Phe Thr Arg His Asn Gly Thr Gly
    370                 375                 380

Gly Lys Ser Ile Tyr Gly Glu Lys Phe Asp Asp Glu Asn Phe Ile Leu
385                 390                 395                 400

Lys His Thr Gly Pro Gly Ile Leu Ser Met Ala Asn Ala Gly Pro Asn
                405                 410                 415

Thr Asn Gly Ser Gln Phe Phe Ile Cys Thr Ala Lys Thr Glu Trp Leu
            420                 425                 430

Asp Gly Lys His Val Val Phe Gly Lys Val Lys Glu Gly Met Asn Val
        435                 440                 445

Val Glu Ala Met Glu Arg Phe Gly Cys Arg Tyr Gly Lys Thr Ser Lys
    450                 455                 460

Lys Ile Thr Ile Ala Asp Cys Gly Gln Leu
465                 470

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gtgactttgc agaatccaaa aacc                                            24

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ggcaatgtcg aagaacacag tagg                                            24

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
```

```
ggttccaaag acagcagaa                                                19
```

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8

```
ttccctgatg tgatactttg                                               20
```

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9

```
atggtcaacc ccaccgtgtt                                               20
```

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10

```
tctgtgaaag caggaaccc                                                19
```

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11

```
ccacatcgct cagacaccat                                               20
```

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12

```
ggcaacaata tccactttac cagagt                                        26
```

<210> SEQ ID NO 13
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13

```
gatccccggg ttcctgcttt cacagattca agagatctgt gaaagcagga accctttttg   60
```

<210> SEQ ID NO 14
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
agcttttcca aaagggttcc ctgctttcac agatctcttg aatctgtgaa agcaggaacc    60
cggg                                                                64

<210> SEQ ID NO 15
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gatccccgac tgagtggttg gatggcttca agagagccat ccaaccactc agtcttttg    60 gaaa                                                                64

<210> SEQ ID NO 16
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
agcttttcca aaagactga gtggttggat ggctctcttg aagccatcca accactcagt    60
cggg                                                                64

<210> SEQ ID NO 17
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gatccccgca tgtggtcttt ggcaaggtgt tcaagagaca ccttgccaaa gaccacatgc    60
tttttggaaa                                                          70

<210> SEQ ID NO 18
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
agcttttcca aaaagcatgt ggtctttggc aaggtgtctc ttgaacacct tgccaaagac    60
cacatgcggg                                                          70

<210> SEQ ID NO 19

```
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gatccccgca tgaatattgt ggaggccatg gttcaagaga ccatggcctc cacaatattc      60 atgcttttg gaaa                                                        74

<210> SEQ ID NO 20
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
agcttttcca aaaagcatga atattgtgga ggccatggtc tcttgaacca tggcctccac      60
aatattcatg cggg                                                       74

<210> SEQ ID NO 21
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gatccccgat caccattgct gactgtgttc aagagacaca gtcagcaatg gtgatctttt      60
tggaaa                                                                66

<210> SEQ ID NO 22
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
agcttttcca aaaagatcac cattgctgac tgtgtctctt gaacacagtc agcaatggtg      60
atcggg                                                                66

<210> SEQ ID NO 23
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gatcccctct gtgctctcgc tgcagtttca agagaactgc agcgagagca cagatttttg      60
gaaa                                                                  64

<210> SEQ ID NO 24
<211> LENGTH: 64
<212> TYPE: DNA
<213> ORGANISM: Artificial Sequence
<220> FEATURE:
<223> OTHER INFORMATION: Description of Artificial Sequence: Synthetic
```

-continued oligonucleotide

<400> SEQUENCE: 24
agcttttcca aaaatctgtg ctctcgctgc agttctcttg aaactgcagc gagagcacag     60
aggg     64

<210> SEQ ID NO 25
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
gatcccccgt acgcggaata cttcgattca agagatcgaa gtattccgcg tacgttttg     60 gaaa     64

<210> SEQ ID NO 26
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
agcttttcca aaaacgtacg cggaatactt cgatctcttg aatcgaagta ttccgcgtac     60
gggg     64

<210> SEQ ID NO 27
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
tttggttata aaggcagctg tttccatagg attattcca     39

<210> SEQ ID NO 28
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
tggaataatc ctatggaaac agctgccttt ataaccaaa     39

<210> SEQ ID NO 29
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
acgtggatcc atggtcaacc ccaccgtgtt     30

<210> SEQ ID NO 30
<211> LENGTH: 34

-continued

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
acgtgaattc ttattagagt tgtccacagt cagc                                  34

<210> SEQ ID NO 31
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
acgtgaattc ttattcgagt tgtccacagt cagc                                  34

<210> SEQ ID NO 32
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
acgtggatcc gccatggctt ccagaatcct ggtc                                  34

<210> SEQ ID NO 33
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
acgtgaattc ttattaggct gatgctacaa ggtccca                               37

<210> SEQ ID NO 34
<211> LENGTH: 142
<212> TYPE: DNA
<213> ORGANISM: Aotus trivirgatus

<400> SEQUENCE: 34
agccgacaga agtccaacgc tactggggta aggagaaatc acattattat aagccaccca      60
gtatgattat ctttatcttt taagaatttt atgttctggc tttgcagacg ccgccgcctg     120
ggaccttgta gcatcagcca tg                                              142

<210> SEQ ID NO 35
<211> LENGTH: 92
<212> TYPE: DNA
<213> ORGANISM: Homo sapiens

<400> SEQUENCE: 35
agctgacaga tgtccgacgc tactggggta aggagaagtc acattatcat aagccaccct      60
gcggcttatc attattatta tctttatctt tt                                   92

<210> SEQ ID NO 36
<211> LENGTH: 231
<212> TYPE: DNA
<213> ORGANISM: Aotus trivirgatus
```

-continued

```
<400> SEQUENCE: 36
aataaagact aaataacaaa aaaaaaaaaa aaaagaattt tatgttctct attaggtctc      60
atgttttaag atttatattt cttcttccag cacacacata acctaccctt ccttataact     120
tctgaacaag gttccttcca gttttctttc aaggctttat taagatttct ctcatataat     180 gttatcccctt acctgacctg ttaatttttt tacagctcat gtgacactgg t             231

<210> SEQ ID NO 37
<211> LENGTH: 210
<212> TYPE: DNA
<213> ORGANISM: Homo sapiens

<400> SEQUENCE: 37
agaattttat gttctctatt aggctcatgt tttaagattt atgattctcc ttccaagaca      60
cacataactt acccctcctt ataacttcta aacaaggttc ctcccagttt tctctcaagt     120
ctttatcaag atttctctca tatcacaaaa aagttacatt atatcccctta gctgacctgt    180 taatttttct acagttgatg tgacagtggc                                      210
```

POLYNUCLEOTIDE ENCODING A TRIM-CYP POLYPEPTIDE, COMPOSITIONS THEREOF, AND METHODS OF USING SAME

This application claims priority to and is a Divisional Application of U.S. application Ser. No. 11/650,384 filed Jan. 5, 2007, which is a continuation of PCT International Application No. PCT/US05/023803, filed on Jul. 6, 2005. This application claims priority to U.S. Ser. No. 60/585,925, filed on Jul. 6, 2004. These documents are hereby incorporated by reference in their entireties.

The invention disclosed herein was made with Government support under NIH Grant No. RO1 A1036199-011 from the Department of Health and Human Services. Accordingly, the U.S. Government has certain rights in this invention.

This patent disclosure contains material that is subject to copyright protection. The copyright owner has no objection to the facsimile reproduction by anyone of the patent document or the patent disclosure, as it appears in the U.S. Patent and Trademark Office patent file or records, but otherwise reserves any and all copyright rights.

Throughout this application, patent applications, published patent applications, issued and granted patents, texts, and literature references are cited. The disclosures of these publications in their entireties are hereby incorporated by reference into this application.

BACKGROUND OF THE INVENTION

In Old World primates, TRIM5-α confers a potent block to human immunodeficiency virus type 1 (HIV-1) infection that acts after virus entry into cells (1-5). (References are listed in numerical order at the end of the specification, and are all incorporated by reference in their entireties for all purposes.) Cyclophilin A (CypA) binding to viral capsid protects HIV-1 from a similar activity in human cells (4, 6-8). Among New World primates, only owl monkeys exhibit post-entry restriction of HIV-1 (1). Paradoxically, the barrier to HIV-1 in owl monkey cells is released by capsid mutants or drugs that disrupt capsid interaction with CypA (4). HIV-1 infection is a serious problem throughout the world and there is a great need for a composition that will prevent infection of a subject by HIV-1 and for a composition that treats or ameliorates the effects of HIV-1 infection in humans.

SUMMARY OF THE INVENTION

The present invention provides an isolated nucleic acid which comprises consecutive nucleotides having a sequence selected from the group consisting of: SEQ ID NO:1 (TRIM-Cyp sequence), SEQ ID NO:2 (*Aotus* TRIM5 Locus (partial genomic sequence)), SEQ ID NO:3 (OMK CypA cDNA), and a variant of any one of the SEQ ID NOS having at least about 50% identity to the SEQ ID NO, and encoding a polypeptide having both TRIM activity and cyclophilin activity. The invention provides for an isolated nucleic acid which comprises consecutive nucleotides having a sequence complementary to the nucleic acids shown in SEQ ID NOS: 1-3. In one embodiment, the invention provides for a nucleic acid which is a variant that has at least about 55%, 60%, 70%, 75%, 80%, 85%, 90%, 95% or 99% identity to any one of SEQ ID NO: 1, 2 or 3, as determined by analysis with a sequence comparison algorithm. The invention also provides for an isolated nucleic acid that hybridizes to such a nucleic acid under high stringency, moderate stringency, or low stringency.

The invention provides for an isolated nucleic acid encoding a polypeptide comprising consecutive amino acids having a sequence comprising SEQ ID NO: 4. The invention also provides for an isolated polypeptide encoded by any of the aforementioned nucleic acids. The invention provides for a purified polypeptide substantially identical to the described polypeptides as determined by analysis with a sequence comparison algorithm or FASTA version 3.0t78 using default parameters. In one embodiment, the invention provides for a polypeptide having the amino acid sequence of SEQ ID NO:4.

The invention provides for an isolated polynucleotide encoding a TRIM-cyclophilin fusion protein. In one embodiment the polynucleotide encodes a polypeptide comprising the amino acid sequence of SEQ ID NO:4. In another embodiment, the polynucleotide encodes a polypeptide consisting essentially of the amino acid sequence of SEQ ID NO:4. In another embodiment, the polynucleotide encodes a polypeptide comprising a sequence that is at least 60%, 65%, 70%, 75%, 80%, 85%, 90%, 95%, or 99% identical to SEQ ID NO:4 and the polypeptide has the function of TRIM and specifically binds a capsid protein of HIV.

The invention provides for a purified antibody that specifically binds to a polypeptide of the invention. In one embodiment, the antibody is a polyclonal antibody, a monoclonal antibody, or a chimeric antibody. In another embodiment, the antibody specifically binds to the protein encoded by any of the aforementioned polynucleotides.

The invention provides for a method of producing a polypeptide of the invention which comprises: (a) introducing a nucleic acid encoding the polypeptide into a host cell under conditions that permit expression of the polypeptide by the host cell, and (b) recovering the polypeptide.

The invention also provides for a replicable nucleic acid vector, which comprises a nucleic acid of the invention. In one embodiment, the vector comprises a viral vector or a retroviral vector. In another embodiment, the vector is an adenovirus vector, a retroviral vector, or an adeno-associated viral (AAV) vector. In another embodiment, the invention provides for a host organism comprising the replicable vector of the invention. In one embodiment, the host is a prokaryote, a eukaryote, or a fungus.

The invention also provides for a method for preparing a pharmaceutical composition which comprises admixing a polypeptide or a fragment thereof of the invention, thereby preparing the pharmaceutical composition. In one embodiment, the pharmaceutical composition comprises a nucleic acid of the invention, a polypeptide of the invention, or a vector of the invention, and a carrier.

In one embodiment, the invention provides for a method for treating a subject suffering from a disease or condition, which comprises administering to the subject a nucleic acid of the invention, a polypeptide of the invention, a vector of the invention, or a pharmaceutical composition of the invention.

The invention provides for a method for treating a subject suffering from a disease or a condition, which comprises administering to the subject a polypeptide or a fragment thereof of the invention, so as to treat the subject.

The invention provides for a method for preventing retroviral infection of a subject, or for treating a subject with retroviral infection, which comprises administering to the subject a pharmaceutical composition of the invention.

The invention provides for a method for treating or preventing a viral infection of a cell which comprises introducing a TRIM-Cyp fusion polypeptide into the cell. In one embodiment, the introducing comprises transfection of a polynucleotide encoding a TRIM-Cyp fusion polypeptide, transduction, viral-mediated introduction, or liposome-mediated introduction. In another embodiment, the viral infection is an HIV infection, an HTLV infection, a pox virus infection, a retrovirus infection, a malaria infection, a hepatitis C virus, a hepatitis B virus, or a vaccinia virus infection. In another embodiment, the pox virus is small pox.

The invention provides a method for treating HIV infection or preventing HIV infection of a subject which comprises introducing into cells of the subject a TRIM-Cyp polypeptide. In one embodiment, the TRIM-Cyp polypeptide binds to a capsid protein of the HIV and subsequently degrades the HIV, thereby treating or preventing HIV infection in the subject.

The invention also provides a peptidomimetic comprising an amino acid sequence substantially identical to the amino acid sequence of a polypeptide of the invention and wherein the peptidomimetic comprises TRIM function and cyclophilin function.

The invention provides for a stem cell comprising a nucleic acid of the invention, wherein the nucleic acid is part of the genome of the stem cell.

The invention provides for a method of imparting resistance to HIV to a cell or a subject which comprises administering to the cell or to the cells of the subject a nucleic acid of the invention, a vector of the invention, or a polypeptide of the invention in an amount effective to impart resistance to HIV infection of cells in the subject.

The invention provides for a therapeutic composition comprising a nucleic acid of the invention, a polypeptide of the invention, or a peptidomimetic of the invention, and a therapeutically acceptable carrier. In one embodiment, the carrier comprises a vector, a liposome, or a viral vector.

The invention provides for a method of ex vivo gene therapy which comprises: (a) removing bone marrow cells from a subject; (b) transfecting the removed bone marrow cells with a nucleic acid or vector of the invention in vitro; and (c) transplanting the transfected bone marrow back into the subject.

The invention provides for a method for reducing viral burden or load in a subject infected by a virus which comprises administering to the subject a nucleic acid of the invention, a polypeptide of the invention, or a vector of the invention.

The invention provides for a topical composition for prevention or treatment of a viral infection which comprises a nucleic acid of the invention or a polypeptide of the invention, and a topical carrier. In one embodiment, the composition is for use on the skin, in the vagina, in the nose, in the mouth, or on any skin or muscosal surface.

The invention also provides for a method for reducing transposition events in a genome of a cell which comprises introducing into the cell a polynucleotide encoding TRIM-cyclophilin A fusion protein, or the protein encoded by the polynucleotide, so as to inhibit L1 elements and reduce transposition events in a cell.

BRIEF DESCRIPTION OF THE FIGURES

The present invention is now illustrated in connection with the accompanying drawings. The invention may be better understood by reference to one or more of these drawings in combination with the detailed description of the specific embodiments presented herein. The invention is not to be construed as limited to the embodiments disclosed, but it is to be understood that these are non-limiting examples of the invention disclosed.

FIGS. 2a-2f. Owl monkey cells express a TRIM5-CypA fusion protein that blocks HIV-1 infection. a, Predicted amino-acid sequence of 54-kD TRIMCyp protein. (SEQ ID NO: 4) TRIM5 segment highlighted in grey with domains indicated above; CypA segment highlighted in black. b, Immunoblot of 293T cells transfected with TRIMCyp expression vector, probed for TRIM5 and CypA. c, d, RT-PCR for TRIMCyp, CypA or TRIM5-α in OMK, human HeLa and Jurkat, and macaque FRhK4 cells (c), and PBMC from two *Aotus nancymaae* monkeys (d). e, Amplification plot of real time RT-PCR. The green curves show undiluted and threefold serial dilutions of $OMK_{MH-Luc}$ cDNA; the black curve is undiluted $OMK_{MH-CypA-147}$ cDNA; the yellow curves are no RT controls. (RT is 'no reverse transcriptase', Rn is 'normalized reporter signal' and 'R' should be '$R^2$' and is the correlation coefficient for the diluted samples.) GAPDH amplification curves (not shown) were identical between samples. f, $OMK_{MH-CypA-147}$ cells transduced with the indicated RNAi-resistant cDNAs and infected with HIV-1.

FIGS. 4a-4c. TRIMCyp arose from retrotransposition of CypA cDNA into TRIM5. a, Part of the owl monkey TRIM5 locus showing a complete, processed CypA cDNA inserted after exon 7. b, c, TRIM5 genomic sequence flanking the 5' end (b) or the 3' end (c) of the CypA insertion aligned with homologous human sequence. TRIMCyp exons and the region homologous to human exon 8 are in capital letters, introns in lower case, and the CypA cDNA insertion highlighted in grey. The 'natural' CypA start codon, the CypA/TRIMCyp poly-adenylation signal and poly-A tail are underlined. The insertion is flanked by a 16-bp target site duplication (TSD), highlighted in black. At, *Aotus trivirgatus*. Hs, *Homo sapiens*.

FIGS. 7a-7c. TRIMCyp and TRIM5α$_{rh}$ abrogate the antiviral activity of endogenous TRIM5α$_{hu}$. (a) TE671 cells expressing the indicated LPCX derived constructs were infected with GFP-expressing B-MLV and N-MLV vectors at multiple doses. Cells were infected in the presence or absence of As$_2$O$_3$ (3 μM). Two days later, the percentage of infected cells was determined by FACS. (b) OMK cells were transduced with MIG (Vect) or with MIG-TRIM5α$_{hu}$ (T5hu) and challenged with DsRed-expressing N-MLV or B-MLV vectors. Two days later, the percentage of infected cells was determined by FACS. (c) OMK/MIG and OMK/MIG-T5hu cells were challenged with HIV-1-derived, DsRed-expressing CSRW vectors in the presence or absence of Cyclosporine A (2.5 μM).

DETAILED DESCRIPTION

Figures 1A, 1B, 1C, 1D, 1E, 1F:
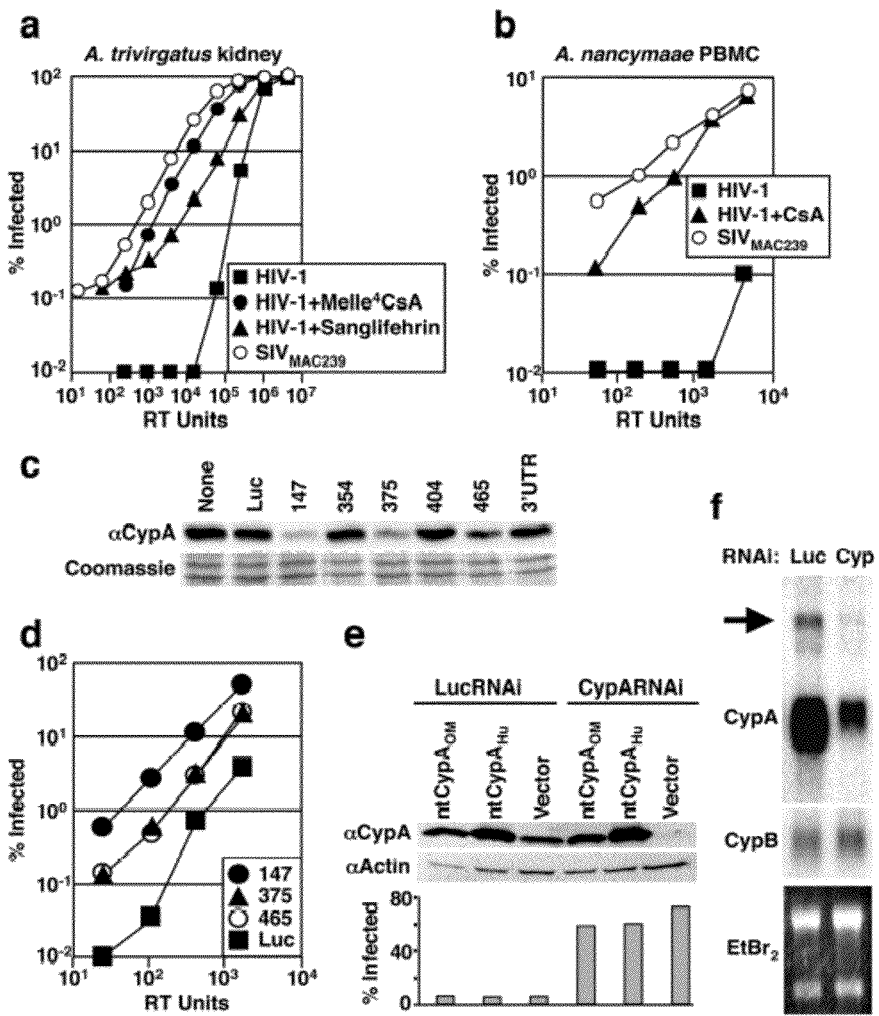
FIGS. 1a-1f. A CypA homologue is required for owl monkey restriction of HIV-1. a, b, *Aotus trivirgatus* OMK cells (a) or *Aotus nancymaae* peripheral blood mononuclear cells (b) were infected with GFP-transducing virions in the presence of CypA-binding drugs. GFP-positive cells were counted by flow cytometry. (RT units are reverse transcriptase units) c, d, OMK cells were transduced with retroviruses delivering shRNAs targeting CypA mRNA at the indicated nucleotide positions. Lysates were immunoblotted (c) and cells were challenged with HIV-1/GFP (d). After antibody detection, the membrane was Coomassie-stained and a representative section is shown as a loading control. Luc is the control shRNA targeting luciferase. e, OMK cells transduced with shRNA-147 were selected after transfection with non-targetable-CypA expression vectors (human or owl monkey) and immunoblotted (top), or infected with HIV-1/GFP (bottom). f, Northern blot of total cytoplasmic RNA from shRNA-147- or shRNA-Luc-treated OMK cells, probed with CypA and CypB cDNA. The arrow indicates a ~2-kb, RNAi-responsive mRNA that hybridizes to CypA. $EtBr_2$, ethidium bromide.

The following sequences are provided by this invention:

```
                                                        SEQ ID NO: 1
(AY646198)-TRIMCyp cDNA
TGCAGGCCCCTGGATTGAGAATATAAACAACAATTCTTATTATCCCTTTTACTGG

TTTGCACGGGGAGAGAGAAGCCAAAGACCTGACTGGGATCTGTGAGCAAGAGGA

GCCTCAGCAGCCAGGACAGGCAAGAGTAGTGGAGCAGCTACTATGGCTTCCAGA

ATCCTGGTCAATATAAAGGAGGAGGTGACCTGCCCCATCTGCCTGGAACTCCTGA
```

-continued

```
CAGAACCCCTGAGCCTGGACTGTGGCCATAGCTTCTGCCAAGCATGCATCACTGC

AAATCACAAAAAGTCTATGCCACACCAAGGAGAGAGAAGCTGCCCTTTGTGCCG

GATCAGTTACTCGTCTGAGAACCTGCGGCCTAATCGGCATTTGGTCAACATAGTG

GAGAGGCTCAGGGAGGTCATGCTGAGCCCAGAGGAGGGGCAGAAGGTTGATCA

CTGTGCACACCATGGAGAGAAACTTGTACTCTTCTGTCAGCAGGATGGAAATGTC

ATTTGCTGGCTTTGTGAGCGGTCTCAAGAACACCGTGGGCACCAGACATTCCTTG

TGGAGGAGGTTGCACAGAAATACCGAGAAAGCTCCAGGTAGCTCTGGAGATGA

TGAGGCAGAAGCAGAAGGATGCTGAAAAGTTGGAAGCTGACGTCAGAGAAGAG

CAAGCTTCCTGGAAGATTCAAATACAAAATGACAAAACCAACATCATGGCAGAG

TTTAAAAAACGGAGAGACATCCTGGACTGTGAGGAGAGCAAAGAGTTGCAAAAC

CTGGAGAAGGAGGAGAAAAACATTCTGAAAAGACTTGTACAGTCTGAAAATGAC

ATGGTGCTGCAGACCCAGTCCGTGAGAGTGCTCATCTCAGATCTGGAGCATCGCC

TGCAGGGGTCAGTGATGGAGCTGTTACAGGGTGTGGATGGTGTCATAAAAAGGA

TTGAGAAAGTGACTTTGCAGAATCCAAAAACCTTTCTTAATGAAAAAAGGAGAA

TATTTCAAACTCCTGATCTGAAAGGAACACTACAAGTGTTTAAAGAGCCGACAG

AAGTCCAACGCTACTGGGACGCCGCCGCCTGGGACCTTGTAGCATCAGCCATGGT

CAATCCTACTGTGTTCTTCGACATTGCCGTCGATGGCGAGCCCTTGGGCCGCGTC

TCCTTCGAGCTGTTTGCAGACAAGGTTCCAAAGACAGCAGAAAACTTTCGTGCTC

TGAGCACTGGAGAGAAAGGATTTGGTTATAAGGGTTCCTGCTTTCACAGAATTAT

TCCAGGGTTTATGTGTCAGGGTGGTGACTTCACACGCCATAATGGCACTGGTGGC

AAGTCCATCTACGGGGAGAAATTTGATGATGAGAACTTCATCCTAAAGCATACA

GGTCCCGGTATCTTGTCCATGGCAAATGCTGGACCCAACACAAACGGTTCCCAGT

TTTTCATCTGCACTGCCAAGACTGAGTGGTTGGATGGCAAGCATGTGGTCTTTGG

CAAGGTGAAAGAAGGCATGAATGTTGTGGAGGCCATGGAGCGCTTTGGGTGCAG

GTATGGCAAGACCAGCAAAAAGATCACCATTGCTGACTGTGGACAACTTTAATA

AGTTTGACTTGTGTTTTGTCTTCACCACCAGACCATTCCTTCTGTAGCTCAGGAGA

GCACCCCTCCACCCCATTTGCTCGCAGTATCCTACAATCTGTGCTCTCGCTGCAGT

TCCCTTTGGGTTCCATGTTTTCCTTGTTCCCTTCCATGCCTAGCTGGATTGCAGAG

TTGAGTTTAAGTTTATGATTATGAAATAAAGACTAAATAACAAAAAAAAAAAAA

AAAAAAAAAA
```

SEQ ID NO: 2
(AY646199)-Aotus TRIM5 Locus (partial genomic sequence)

```
TTTCTTAATGAAAAAGGAGAATATTTCAAACTCCTGATCTGAAAGGAACA

CTACAAGTGTTTAAAGGTGAGGAGAGCTGGATCAACTGCGGGGTTGTGGAATGC

AAGTCCCGACTGTGTCAGGGTGCTAAATGGAGAAAAGAGTGTGGTTTCCAAATA

TGGATAGAGGGGATGGGGAAGATGGATATTATCTGCTGCTGATGGGATTATATTT

AATGAGAAATGGCTAGGTGGCTGTTTCACCCTGTCATTCACCAGTTTACTGCCCT

ACCATAGGGCATGCCTACTCTTTCCCTAATCTGGAGAGAAAATGAATTTCAGTGC

TGACTCCTTTTACTTGTATCCAATATTATGCATTTTTATCATTTCAGAGCCGACAG

AAGTCCAACGCTACTGGGGTAAGGAGAAATCACATTATTATAAGCCACCCAGTA

TGATTATCTTTATCTTTTAAGAATTTTATGTTCTGGCTTTGCAGACGCCGCCGCCT
```

-continued

```
GGGACCTTGTAGCATCAGCCATGGTCAATCCTACTGTGTTCTTCGACATTGCCGT

CGATGGCGAGCCCTTGGGCCGCGTCTCCTTCGAGCTGTTTGCAGACAAGGTTCCA

AAGACAGCAGAAAACTTTCGTGCTCTGAGCACTGGAGAGAAAGGATTTGGTTAT

AAGGGTTCCTGCTTTCACAGAATTATTCCAGGGTTTATGTGTCAGGGTGGTGACT

TCACACGCCATAATGGCACTGGTGGCAAGTCCATCTACGGGGAGAAATTTGATG

ATGAGAACTTCATCCTAAAGCATACAGGTCCCGGTATCTTGTCCATGGCAAATGC

TGGACCCAACACAAACGGTTCCCAGTTTTTCATCTGCACTGCCAAGACTGAGTGG

TTGGATGGCAAGCATGTGGTCTTTGGCAAGGTGAAAGAAGGCATGAATGTTGTG

GAGGCCATGGAGCGCTTTGGGTGCAGGTATGGCAAGACCAGCAAAAAGATCACC

ATTGCTGACTGTGGACAACTTTAATAAGTTTGACTTGTGTTTTGTCTTCACCACCA

GACCATTCCTTCTGTAGCTCAGGAGAGCACCCCTCCACCCCATTTGCTCGCAGTA

TCCTACAATCTGTGCTCTCGCTGCAGTTCCCTTTGGGTTCCATGTTTTCCTTGTTCC

CTTCCATGCCTAGCTGGATTGCAGAGTTGAGTTAAGTTTATGATTATGAAATAAA

GACTAAATAACAAAAAAAAAAAAAAAAGAATTTTATGTTCTCTATTAGGTCTC

ATGTTTTAAGATTTATATTTCTTCTTCCAGCACACACATAACCTACCCTTCCTTAT

AACTTCTGAACAAGGTTCCTTCCAGTTTTCTTTCAAGGCTTTATTAAGATTTCTCT

CATATAATGTTATCCCTTACCTGACCTGTTAATTTTTTTACAGCTCATGTGACACT

GGTTCCAAGTCACCCTTCATGTACTGTCATTTCTGAAGATGAGAGACAAGTGAGA

TATCAGAAACGGATATATCAACCATTTCTGAAAGTCAAGTATTTTTGTGGCGTCC

TGGGCTCCCCAAGTATCACATCAGGGAAACATTACTGGGAGGTAGACGTGTCCA

ATAAAAGTGAGTGGATCCTGGGGGTATGTGTTAGCTTGAAGCGCACTGCAAGTT

GTAGTGTTCCAAGAATTGAAAATGATCAACCTAAAAATGGCTACTGGGTTATAG

GGTTACGGAATGCAGATAACTATAGTGCTTTCCAGGATGCAGTTGAATATAGTGA

TTTCCAGGATGGTTCCCGCTCTACTCCTTCTGCTCCTTTGATCGTGCCCCTCTTTAT

GACTATTTGTCCTAATCGTGTTGGAGTTTTCCTAGACTATGAGGCTTGCACTGTCT

CATTCTTCAATGTCACAAACAATGGATTTCTCATCTATAAGTTTTCTAACTGTCAT

TTTTGTTATCCTGTATTTCCATATTTCAGTCCTATGACATGTGAATTACCCATGAC

TCTGTGCTCACCAAGCTCTTGAACTATCTTAAATACTCAGCCGCTTCTTACCCAGG

TGCATCTCATACACCTGAACCTTCAT
```

SEQ ID NO: 3
(AY646200)-OMK CypA cDNA

```
CCTTGTAGCATCAGCCATGGTCAATCCTACCGTGTTCTTCGACATTGCCGT

CGATGGCGAGCCCTTGGGCCGCGTCTCCTTCGAGCTGTTTGCAGACAAGGTTCCA

AAGACAGCAGAAAACTTTCGTGCTCTGAGCACTGGAGAGAAAGGATTTGGTTAT

AAGGGTTCCTGCTTTCACAGAATTATTCCAGGGTTTATGTGTCAGGGTGGTGACT

TCACACGCCATAATGGCACTGGTGGCAAGTCCATCTACGGGGAGAAATTTGATG

ACGAGAACTTCATCCTAAAGCATACAGGTCCCGGTATCTTGTCCATGGCAAATGC

TGGACCCAACACAAACGGTTCCCAGTTTTTCATCTGCACTGTCAAGACTGAGTGG

TTGGATGGCAAGCATGTGGTCTTTGGCAAGGTGAAAGAAGGCATGAATATTGTG

GAGGCCATGGAGCGCTTTGGGTCCAGGAATGGCAAGACCAGCAAGAAGATCACC

ATTGCTGACTGTGGACAACTTTAATAAGTTTGACTTGTGTTTTGTCTTCACCACCA

GACCATTCCTTCTGTAGCTCAGGAGAGCACCCCTCCACCCCATTTGCTCGCAGTA
```

-continued

```
TCCTAAAATCTGTGCTCTCGCTGCAGTTCCCTTTGGGTCCCATGTTTTCCTTGTTCC

CTTCCATGCCTAGCTGGATTGCAGAGTTGAGTTAAGTTTATGATTATGAAATAAA

GACTAAATAACAAAAAAAAAAAAAAAA
```

SEQ ID NO: 4
amino acid sequence of TRIMcyp (FIG. 2A)
```
MASRILVNIKEEVTCPICLELLTEPLSLDCGHSFCQACITANHKKSMPHQGERS

CPLCRISYSSENLRPNRHLVNIVERLREVMLSPEEGQKVDHCAHHGEKLVLFCQQDG

NVICWLCERSQEHRGHQTFLVEEVAQKYREKLQVALEMMRQKQKDAEKLEADVRE

EQASWKIQIQNDKTNIMAEFKKRRDILDCEESKELQNLEKEEKNILKRLVQSENDMV

LQTQSVRVLISDLEHRLQGSVMELLQGVDGVIKRIEKVTLQNPKTFLNEKRRIFQTPD

LKGTLQVFKEPTEVQRYWDAAAWDLVASAMVNPTVFFDIAVDGEPLGRVSFELFAD

KVPKTAENFRALSTGEKGFGYKGSCFHRIIPGFMCQGGDFTRHNGTGGKSIYGEKFD

DENFILKHTGPGILSMANAGPNTNGSQFFICTAKTEWLDGKHVVFGKVKEGMNVVE

AMERFGCRYGKTSKKITIADCGQL
```

The invention provides for a newly discovered and isolated nucleic acid or polynucleotide that was isolated from an owl monkey, that comprises the nucleotide sequence of SEQ ID NO:1, 2 or 3, or encodes the polypeptide of SEQ ID NO:4. The polypeptide is a fusion between TRIM and cyclophilin, i.e., TRIMcyp, which acts as an anti-HIV-1 factor.

The invention also provides for nucleic acid variants of any of SEQ ID NO: 1, 2, or 3 having at least about 50% identity to the SEQ ID NO, and encoding a polypeptide having both TRIM activity and cyclophilin activity. The variants may have at least about 55%, 60%, 70%, 75%, 80%, 85%, 90%, 95%, or 99% identity to the SEQ ID NO. Techniques for determining sequence identity are well known to one skilled in the art, and include, for example, analysis with a sequence comparison algorithm or FASTA version 3.0t78 using default parameters.

The invention also provides for an isolated nucleic acid which comprises consecutive nucleotides having a sequence complementary to the nucleic acids comprising the nucleotide sequence of SEQ ID NO:1, 2, or 3, or variants of at least about 50% identity thereof. The invention also provides for an isolated nucleic acid encoding a polypeptide comprising consecutive amino acids having a sequence comprising SEQ ID NO:4. Also provided by the invention is an isolated nucleic acid that hybridizes to a nucleic acid of the invention under conditions of high stringency, moderate stringency, or low stringency.

The invention further provides for an isolated polypeptide encoded by an isolated nucleic acid of the invention. Purified polypeptides substantially identical to the isolated polypeptide, as determined by analysis with a sequence comparison algorithm or FASTA version 3.0t78 using default parameters, are also included in the invention.

The present invention also provides for methods of making cells resistant to HIV-1 infection. The present invention provides for an isolated fusion protein between TRIM5 and cyclophilin A which was discovered and isolated from Owl monkey, which is a species of primate from South America that are resistant to HIV-1 infection. This newly discovered TRIM-cyclophilin fusion protein provides the Owl monkey with its resistance to HIV. The cyclophilin A part of the fusion molecule specifically binds to the HIV-1 capsid protein once HIV-1 enters the cell. The TRIM5 part of the fusion protein acts as TRIM 5 alone has been characterized, causing the degradation of the substance bound to the cyclophilin A portion of the fusion protein, namely the degradation of HIV-1. Thus, the fusion protein has coupled a specific binding tropism, i.e., the binding of cyclophilin to capsid of HIV-1, with the degradation activity of TRIM5, to create a sort of Trojan horse.

The cyclophilin part of the fusion protein is highly conserved among different species. Cyclophilin is a protein that is present in yeast and in humans. It plays a role in protein-folding and in the biological response to the immunosuppressive drug cyclosporine. The TRIM5 part of the fusion protein is highly variable from one species to another.

The invention provides a TRIM-cyclophilin fusion protein encoded by the amino acid sequence of SEQ ID NO:4. The invention also provides a TRIM-cyclophilin fusion protein encoded by an isolated polynucleotide of the invention. The isolated polynucleotide may encode a polypeptide comprising, consisting essentially of, or comprising a sequence that is at least 60%, 70%, 75%, 80%, 85%, 90%, 95%, or 99% identical to, SEQ ID NO:4, and wherein the polypeptide has the function of TRIM and specifically binds a capsid protein of HIV.

The invention further provides for a purified antibody that specifically binds to a polypeptide of the invention or to a protein encoded by a polynucleotide of the invention. The antibody may be a polyclonal antibody, a monoclonal antibody, or a chimeric antibody. Polyclonal antibodies may be obtained by procedures which are well known to the skilled artisan, including injecting purified fusion protein into various animals and isolating the antibodies produced in the blood serum. The antibodies may be monoclonal antibodies whose method of production is well known to the art, including, for example, injecting purified fusion protein into a mouse, isolating the spleen cells producing the anti-serum, fusing the cells with tumor cells to form hybridomas and screening the hybridomas.

Methods for producing the polypeptides of the invention include introducing a nucleic acid encoding the polypeptide into a host cell under conditions that permit expression of the polypeptide by the host cell, and recovering the peptide. A nucleic acid may be introduced into a host cell, for example, with a replicable nucleic acid vector, such as a viral vector, a retroviral vector, an adenovirus vector, or an adeno-associated viral (AAV) vector. Provided for in the invention is a replicable nucleic acid vector comprising a nucleic acid of the invention, and a host organism comprising the replicable nucleic acid vector. Suitable host organisms include a prokaryote, a eukaryote, or a fungus.

The invention provides for a host cell comprising the recombinant expression construct encoding the TRIMCyp fusion protein as described herein. In another embodiment of the invention, the host cell is stably transformed with the recombinant expression construct described herein. In one embodiment the host cell is a bone marrow cell of a subject. In another embodiment of the invention, the cell is an immortalized cell.

A nucleic acid, a polypeptide, or a nucleic acid vector of the invention may be used to prepare pharmaceutical compositions of the invention. Methods for preparing a pharmaceutical composition include admixing a polypeptide of the invention or a fragment thereof.

The pharmaceutical composition further comprises a pharmaceutically acceptable carrier. The carrier comprises a diluent. The carrier may also comprise an appropriate adjuvant, a herpes virus, an adenovirus, a liposome, a microencapsule, a polymer encapsulated cell or a retroviral vector. The pharmaceutically acceptable carrier may be an aerosol, intravenous, oral or topical carrier.

A nucleic acid, a polypeptide, a nucleic acid vector, or a pharmaceutical composition of the invention is suitable for treating a subject suffering from a disease or condition, such as a retroviral infection. In one embodiment, the invention provides for methods of preventing retroviral infection in a subject, or for treating a subject with a retroviral infection, by administering to the subject a pharmaceutical composition of the invention. In another embodiment, the invention provides for methods of reducing viral burden, or load, in a subject infected by a virus by administration of a nucleic acid, a polypeptide, or a nucleic acid vector of the invention, to the subject.

The invention provides for methods of gene therapy of subjects for the prevention or treatment of viral infection comprising administering to the subject an effective amount of a pharmaceutical composition comprising, or consisting essentially of, a polynucleotide encoding a fusion protein having cyclophilin fused to a TRIM polypeptide, wherein the subject's cells takes up the polynucleotide or polypeptide such that the fusion protein is present in cells of the subject, so as to prevent or treat viral infection in the subject. In one embodiment, the treated subject has a reduced viral load, or burden. In one embodiment of this invention, the administering is via an autologous bone marrow transplant to the subject, where the polynucleotides coding for the fusion protein is transfected into the bone marrow cells ex vivo and then replaced into the subject. In this case, the bone marrow cells returned to the subject will have taken up (been transduced) the nucleic acid encoding the fusion protein.

Viral infections that may be treated or prevented by introducing a TRIM-Cyp fusion polypeptide into the subject's cells include an HIV infection, a human T-cell lymphotrophic virus (HTLV) infection, a pox virus infection, a retrovirus infection, a malaria infection, a hepatitis C virus infection, a hepatitis B virus infection, or a vaccinia virus infection. In one embodiment, the pox virus is small pox.

The present invention provides for the TRIMCyp fusion protein which combines a specific binding activity (specific for HIV-1 capsid protein) and a killing activity (TRIM activity, like ubiquitin). In this way, the HIV-1 is degraded in the cell.

The invention provides methods for treating HIV infection or preventing HIV infection of a subject by introducing a TRIM-Cyp fusion polypeptide into the subject's cells. The TRIM-Cyp polypeptide binds to a capsid protein of the HIV and subsequently degrades the HIV, thereby treating or preventing the HIV infection in the subject. Resistance to HIV may also be imparted to a subject or to the cells of a subject by administering to the cells of the subject a nucleic acid, a polypeptide, or a nucleic acid vector of the invention.

The invention also provides for a peptidomimetic comprising an amino acid sequence substantially identical to the amino acid sequence of a polypeptide of the invention. As used herein a "peptidomimetic" refers to a chemical compound that mimics the biological activity of a peptide. In one embodiment of the invention, a peptidomimetic comprises TRIM function and cyclophilin function.

A peptidomimetic, a nucleic acid, or a polypeptide of the invention is suitable for preparing a therapeutic composition of the invention. The therapeutic composition further comprises a therapeutically acceptable carrier. The carrier may comprise a vector, a liposome, or a viral vector.

The invention further provides a stem cell comprising a nucleic acid of the invention, wherein the nucleic acid is part of the genome of the stem cell. As used herein a "stem cell" refers to an undifferentiated cell in the bone marrow that has the ability both to multiply and to differentiate into a specific, specialized cell, such as a blood cell. In one embodiment, human hematopoietic stem cells are mobilized from the bone marrow of an HIV-1 infected subject, the cells are transduced in vitro with vectors expressing TRIMCyp, and the cells are injected back into the patient as an auto-transplant.

Also provided in the invention is a method for reducing transposition events in a genome of a cell. The method comprises introducing into the cell a polynucleotide encoding a TRIM-cyclophilin A fusion protein, or the protein encoded by the polynucleotide, so as to inhibit LINE 1 (L1) elements and reduce transposition elements in the cell. As used herein a "LINE" refers to a Long Interspersed Element. Functional L1 elements are about 6,500 bp in length and encode three proteins, including an endonuclease that cuts DNA and a reverse transcriptase that makes a DNA copy of an RNA transcript. L1 activity proceeds as follows: RNA polymerase II transcribes the L1 DNA into RNA; the RNA is translated by ribosomes in the cytoplasm into the proteins; the proteins and RNA join together and reenter the nucleus; the endonuclease cuts a strand of "target" DNA, often in the intron of a gene; and the reverse transcriptase copies the L1 RNA into L1 DNA which is inserted into the target DNA forming a new L1 element there.

For the purposes of this invention, "administration" means any of the standard methods of administering a pharmaceutical composition known to those skilled in the art. Examples include, but are not limited to, intravenous, intraperitoneal or intramuscular administration, in vitro gene therapy via adenoviral vector or other vector (liposome), ex vivo gene therapy, oral, and inhalation. In another embodiment of the invention, the administering is carried out via injection, oral administration, or topical administration. In one embodiment of this invention, the subject is a mammal, e.g., a mouse or a human. Preferably, the mammal is a human. In another embodiment of the invention, the "introducing" or administering is carried out by a means selected from the group consisting of transduction, viral-mediated introduction, adenovirus infection, liposome-mediated transfer, topical application to the cell, and microinjection. In another embodiment of the invention, the carrier is an aqueous carrier, a liposome, a vector, a viral vector, or a lipid carrier.

Provided by the invention is a topical composition for prevention or treatment of a viral infection which comprises a nucleic acid or a polypeptide of the invention. The topical composition further comprises a topical carrier, and may be used on the skin, in the vagina, in the nose, in the mouth, or on any skin or mucosal surface.

As used herein "nucleic acid molecule" includes both DNA and RNA and, unless otherwise specified, includes both double-stranded and single-stranded nucleic acids. Also included are hybrids such as DNA-RNA hybrids. Reference to a nucleic acid sequence can also include modified bases as long as the modification does not significantly interfere either with binding of a ligand such as a protein by the nucleic acid or Watson-Crick base pairing.

Two DNA or polypeptide sequences are "substantially homologous" when at least about 80% (preferably at least about 90%, and most preferably at least about 95%) of the nucleotides or amino acids match over a defined length of the molecule. As used herein, "substantially homologous" also refers to sequences showing identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., *Molecular Cloning: A Laboratory Manual*, Cold Springs Harbor Laboratory, 2nd ed., Cold Springs Harbor, N.Y. (1989).

A DNA "coding sequence" or a "nucleotide sequence encoding" a particular protein, is a DNA sequence which is transcribed and translated into a polypeptide in vivo or in vitro when placed under the control of appropriate regulatory sequences. The boundaries of the coding sequence are determined by a start codon at the 5'-(amino) terminus and a translation stop codon at the 3'-(carboxy) terminus A coding sequence can include, but is not limited to, prokaryotic sequences, cDNA from eukaryotic mRNA, genomic DNA sequences from eukaryotic (e.g., mammalian) sources, viral RNA or DNA, and even synthetic nucleotide sequences. A transcription termination sequence will usually be located 3' to the coding sequence.

"Operably linked" refers to an arrangement of nucleotide sequence elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

A cell has been "transformed" by exogenous DNA when such exogenous DNA has been introduced inside the cell membrane. Exogenous DNA may or may not be integrated (covalently linked) into chromosomal DNA making up the genome of the cell. In prokaryotes and yeasts, for example, the exogenous DNA may be maintained on an episomal element, such as a plasmid. In eukaryotic cells, a stably transformed cell is generally one in which the exogenous DNA has become integrated into the chromosome so that it is inherited by daughter cells through chromosome replication, or one which includes stably maintained extrachromosomal plasmids. This stability is demonstrated by the ability of the eukaryotic cell to establish cell lines or clones comprised of a population of daughter cells containing the exogenous DNA.

The present invention encompasses use of virus based vectors for transformation or transfection of the TRIMCyp coding region into a cell. In the case of eukaryotic cells, retrovirus or adenovirus based vectors are preferred. Such vectors contain all or a part of a viral genome, such as long term repeats ("LTRs"), promoters (e.g., CMV promoters, SV40 promoter, RSV promoter), enhancers, and so forth. When the host cell is a prokaryote, bacterial viruses or phages are preferred. Exemplary of such vectors are vectors based upon, e.g., lambda phage. In any case, the vector may comprise elements of more than one virus. The resulting vectors are transfected or transformed into a host cell, which may be eukaryotic or prokaryotic. The gene transfer vector of the present invention may additionally comprise a gene encoding a marker or reporter molecule to more easily trace expression of the vector. The gene transfer vector may contain more than one gene encoding the same or different foreign polypeptides or RNAs. The gene transfer vector may be any construct which is able to replicate within a host cell and includes plasmids, DNA viruses, retroviruses, as well as isolated nucleotide molecules. Liposome-mediated transfer of the gene transfer vector may also be carried out in the present invention.

Adenoviruses can be used for transformation or transfection of the nucleic acids of the present invention into cells. Examples of such adenovirus serotypes which can be employed in the present invention are well-known in the art and include more than 40 different human adenoviruses, e.g., Ad12 (subgenus A), Ad3 and Ad7 (Subgenus B), Ad2 and Ad5 (Subgenus C), Ad8 (Subgenus D), Ad4 (Subgenus E), Ad40 (Subgenus F) (Wigand et al, in: Adenovirus DNA, Doerfler, Ed., Martinus Nijhoff Publishing, Boston, pp. 408-441 (1986)). Ad5 of subgroup C is the preferred adenovirus employed in the present invention. This is because Ad5 is a human adenovirus about which a great deal of biochemical and genetic information is known, and it has historically been used for most constructions employing adenovirus as a vector. Also, adenoviral vectors are commercially available, e.g., pCA3 (Microbix Biosystems Inc.). Methods for producing adenovirus vectors are well-known in the art (Berkner et al, Nucleic Acids Res., 11:6003-6020 (1983); van Doren et al, Mol. Cell. Biol., 4:1653-1656 (1984); Ghosh-Choudhury et al, Biochem. Biophys. Res. Commun., 147:964-973 (1987); McGrory et al, Virol., 163:614-617 (1988); and Gluzman et al, in: Eurkaryotic Viral Vectors, Ed. Gluzman, Y. pages 187-192, Cold Spring Harbor Laboratory (1982)). Vectors which can be used in the methods of the present invention include adenoviruses, retroviral vectors, and adeno-associated viral (AAV) vectors. Other virus vectors that may be used for gene transfer into cells include retroviruses such as Moloney murine leukemia virus (MoMuLV); papovaviruses such as JC, SV40, polyoma, adenoviruses; Epstein-Barr Virus (EBV); papilloma viruses, e.g. bovine papilloma virus type I (BPV); vaccinia and poliovirus and other human and animal viruses. Expression can be amplified by placing an amplifiable gene, such as the mouse dihydrofolate reductase (dhfr) gene adjacent to the coding sequence. Cells can then be selected for methotrexate resistance in dhfr-deficient cells. See, e.g. Urlaub et al. (1980) Proc. Natl. Acad. Sci. USA 77:4216-4220; Rungold et al. (1981) J. Mol. and Appl. Genet. 1:165-175.

It may also be desirable to produce mutants or analogs of the proteins of interest. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art. See, e.g., Sambrook et al., *Molecular Cloning: A Laboratory Manual*, Cold Springs Harbor Laboratory, 2nd ed., Cold Springs Harbor, N.Y. (1989).

The constructs can also be used in gene therapy or nucleic acid immunization, to direct the production of the desired gene product in vivo, by administering the expression constructs directly to a subject for the in vivo translation thereof. See, e.g. EPA Publication No. 336,523 (Dreano et al., published Oct. 11, 1989). Alternatively, gene transfer can be accomplished by transfecting the subject's cells or tissues with the expression constructs ex vivo and reintroducing the transformed material into the host. The constructs can be directly introduced into the host organism, i.e., by injection (see International Publication No. WO/90/11092; and Wolff et al., (1990) Science 247:1465-1468). Liposome-mediated gene transfer can also be accomplished using known methods. See, e.g., Hazinski et al., (1991) Am. J. Respir. Cell Mol. Biol. 4:206-209; Brigham et al. (1989) Am. J. Med. Sci. 298:278-281; Canonico et al. (1991) Clin. Res. 39:219 A; and Nabel et al. (1990) Science 249:1285-1288. Targeting agents, such as antibodies directed against surface antigens expressed on specific cell types, can be covalently conjugated to the liposomal surface so that the nucleic acid can be delivered to specific tissues and cells for local administration.

There are several protocols for human gene therapy which have been approved for use by the Recombinant DNA Advisory Committee (RAC) which conform to a general protocol of target cell infection and administration of transfected cells (see for example, Blaese, R. M., et al., 1990; Anderson, W. F., 1992; Culver, K. W. et al., 1991). In addition, U.S. Pat. No. 5,399,346 (Anderson, W. F. et al., Mar. 21, 1995, U.S. Serial No. 220,175) describes procedures for retroviral gene transfer. The contents of these support references are incorporated in their entirety into the subject application. Retroviral-mediated gene transfer requires target cells which are undergoing cell division in order to achieve stable integration hence, cells are collected from a subject often by removing blood or bone marrow. It may be necessary to select for a particular subpopulation of the originally harvested cells for use in the infection protocol. Then, a retroviral vector containing the gene(s) of interest would be mixed into the culture medium. The vector binds to the surface of the subject's cells, enters the cells and inserts the gene of interest randomly into a chromosome. The gene of interest is now stably integrated and will remain in place and be passed to all of the daughter cells as the cells grow in number. The cells may be expanded in culture for a total of 9-10 days before reinfusion (Culver et al., 1991). As the length of time the target cells are left in culture increases, the possibility of contamination also increases, therefore a shorter protocol would be more beneficial.

One way to get DNA into a target cell is to put it inside a membrane bound sac or vesicle such as a spheroplast or liposome, or by calcium phosphate precipitation ($CaPO_4$) (Graham F. and Van der Eb, A., Virology 52:456 1973; Schaefer-Ridder M., et al., Liposomes as gene carriers: Efficient transduction of mouse L cells by thymidine kinase gene. Science 1982; 215:166; Stpyridis J. C., et al., Construction of transferrin-coated liposomes for in vivo transport of exogenous DNA to bone marrow erythroblasts in rabbits. Exp Cell Res 1986; 164:568-572).

A vesicle can be constructed in such a way that its membrane will fuse with the outer membrane of a target cell. The vector of the invention in vesicles can home into the cancer cells. The spheroplasts are maintained in high ionic strength buffer until they can be fused through the mammalian target cell using fusogens such as polyethylene glycol.

Liposomes are artificial phospholipid vesicles. Vesicles range in size from 0.2 to 4.0 micrometers and can entrap 10% to 40% of an aqueous buffer containing macromolecules. The liposomes protect the DNA from nucleases and facilitate its introduction into target cells. Transfection can also occur through electroporation. Before administration, the modified vectors are suspended in complete PBS at a selected density for injection. In addition to PBS, any osmotically balanced solution which is physiologically compatible with the subject may be used to suspend and inject the modified vectors into the host.

For injection, the cell suspension is drawn up into the syringe and administered to anesthetized recipients. Multiple injections may be made using this procedure. The viral suspension procedure thus permits administration of genetically modified vectors to any predetermined site in the skin, is relatively non-traumatic, and allows multiple administrations simultaneously in several different sites or the same site using the same viral suspension. Multiple injections may consist of a mixture of therapeutic genes.

As used in this specification and the appended claims, the singular forms "a," "an" and "the" include plural references unless the content clearly dictates otherwise.

This invention is illustrated in the Example sections that follow. These sections are set forth to aid in an understanding of the invention but are not intended to, and should not be construed to, limit in any way the invention as set forth in the claims which follow thereafter.

Example 1

Cyclophilin A Retrotransposition into TRIM5 Explains Owl Monkey Resistance to HIV-1

Here we show that knockdown of owl monkey CypA by RNA interference (RNAi) correlates with suppression of anti-HIV-1 activity. However, reintroduction of CypA protein to RNAi-treated cells did not restore antiviral activity. A search for additional RNAi targets unearthed TRIMCyp, an RNAi-responsive messenger RNA encoding a TRIM5-CypA fusion protein. TRIMCyp accounts for post-entry restriction of HIV-1 in owl monkeys and blocks HIV-1 infection when transferred to otherwise infectable human or rat cells. It seems that TRIMCyp arose after the divergence of New and Old World primates when a LINE-1 retrotransposon catalysed the insertion of a CypA complementary DNA into the TRIM5 locus. This is the first vertebrate example of a chimaeric gene generated by this mechanism of exon shuffling.

Post-entry restriction of HIV-1 infection is common among Old World monkeys, but owl monkeys are unique among New World primates in exhibiting this phenotype (1). *Aotus trivirgatus* owl monkey kidney cells (OMK) restrict HIV-1 infection, but are permissive for simian immunodeficiency virus (SIV) infection (1). HIV-1 restriction in OMK cells is completely abrogated when the interaction between HIV-1 capsid and the cellular protein cyclophilin A (CypA) is disrupted (4), either by mutations altering capsid or by treatment of target cells with the cyclophilin-binding drug cyclosporine (CsA). This phenotype is the opposite of that seen in most human cells where the capsid-CypA interaction is required for efficient HIV-1 replication (4, 6-9).

The paradoxical response to CsA in OMK cells was investigated further using two other drugs: MeIle$^4$-CsA, a non-immunosuppressive analogue (9), and sanglifehrin, a structurally unrelated compound that also binds cyclophilin (10). As with CsA, treatment of target cells with these compounds permits HIV-1 to infect OMK cells at an efficiency similar to that of SIV (FIG. 1a). Peripheral blood mononuclear cells (PBMC) from a different owl monkey species, Aotus nancymaae, show the same restriction phenotype with respect to SIV, HIV-1 and CsA (FIG. 1b). Identical results were obtained with PBMC from a second animal.

CsA, MeIle$^4$-CsA and sanglifehrin bind cyclophilin family members, but not exclusively CypA. To examine the specific role of CypA, we generated stable OMK cell lines with CypA knockdown by RNAi. Of six CypA-specific small hairpin RNAs (shRNAs), three decreased CypA expression (FIG. 1c). Those shRNA constructs that decreased CypA expression abrogated HIV-1 restriction to a corresponding degree (FIG. 1d).

To determine whether disruption of HIV-1 restriction was due to CypA knockdown, the OMK knockdown cell line with the largest decrease in CypA expression and HIV-1 restriction (OMK$_{MH-CypA-147}$) was transfected with non-targetable CypA cDNAs (ntCypA) bearing silent mutations to make them resistant to the RNAi. A plasmid encoding cell surface H-2K$^K$ was cotransfected so that transfected cells could be enriched using antibodies conjugated to magnetic particles. Although cells selected in this manner were fully restored for CypA expression, they remained deficient for HIV-1 restriction (FIG. 1e). We attempted to restore CypA expression in OMK$_{MH-CypA-147}$ cells several times using different methods, including retroviral transduction of ntCypA cDNA. In all cases, reconstitution of CypA expression did not restore HIV-1 restriction activity.

Off-target spread of RNAi has been reported (11), but this seemed an unlikely explanation for our inability to restore restriction to OMK$_{MH-CypA-147}$ because CypA knockdown with three different RNAi target sequences was associated with loss of restriction. A more plausible explanation seemed to be knockdown of an unknown mRNA homologous to CypA. Multiple screens of OMK cDNA by hybridization or polymerase chain reaction (PCR) yielded only bona fide CypA cDNA. Northern analysis was performed to look for transcripts other than CypA that were decreased by RNAi in these cells. Total cytoplasmic RNA from OMK$_{MH-CypA-147}$, or from control OMK cells treated with RNAi specific for luciferase, was hybridized with CypA coding sequence (FIG. 1f). The dominant CypA transcript (about 750 nucleotides) was significantly reduced in OMK$_{MH-CypA-147}$. Another transcript of approximately 2 kb hybridized to the CypA probe and was also decreased by RNAi against CypA.

To identify the larger transcript detected by northern blot, a size-selected OMK cDNA library (1,700 to 2,500 base pairs, bp) was screened by colony hybridization with a CypA probe. Inserts from four positive colonies were sequenced. Two contained in-frame fusions between TRIM5 (exons 1 to 7) and a complete CypA cDNA. This TRIMCyp cDNA was predicted to encode a 54-kD protein chimaera consisting of the aminoterminal 299 amino acids of TRIM5 and the 165-amino-acid CypA protein linked by 11 amino acids encoded by the CypA 5' untranslated region (UTR) (FIG. 2a). 293T cells transfected with a TRIMCyp cDNA expression vector produced a protein of the expected size that was reactive with both anti-TRIM5 and anti-CypA antibodies (FIG. 2b).

TRIMCyp mRNA was detectable in OMK cells and in PBMC from two Aotus nancymaae monkeys (FIG. 2c, d), but not in the human cell lines Jurkat or HeLa, or in rhesus macaque FRhK4 cells (FIG. 2c). Quantitative reverse transcription (RT)-PCR was used to demonstrate that TRIMCyp expression in the CypA knockdown cells used in FIG. 1e, f was decreased tenfold (FIG. 2e).

To determine whether TRIMCyp was sufficient to restore HIV-1 restriction to CypA knockdown OMK cells, OMK$_{MH-CypA-147}$ were transduced with a pMIG retroviral vector delivering a TRIMCyp cDNA bearing silent mutations that render it resistant to RNAi (ntTRIMCyp). pMIG expresses cDNAs fused to an internal ribosome entry site (IRES)-green fluorescent protein (GFP) cassette, permitting identification of transduced cells by GFP expression. pMIG-transduced OMK$_{MH-CypA-147}$ cells were assayed for their ability to restrict an HIV-1 vector that delivers the DsRed fluorescent protein. OMK$_{MH-CypA-147}$ cells transduced with pMIG-ntTRIMCyp restricted HIV-1, while those transduced with empty vector, or vector delivering ntCypA$_{OM}$, did not (FIG. 2f). Loss of restriction in OMK cells caused by RNAi against CypA (FIG. 1c, d) could therefore be attributed to TRIMCyp knockdown.

Figures 3A, 3B, 3C, 3D, 3E:
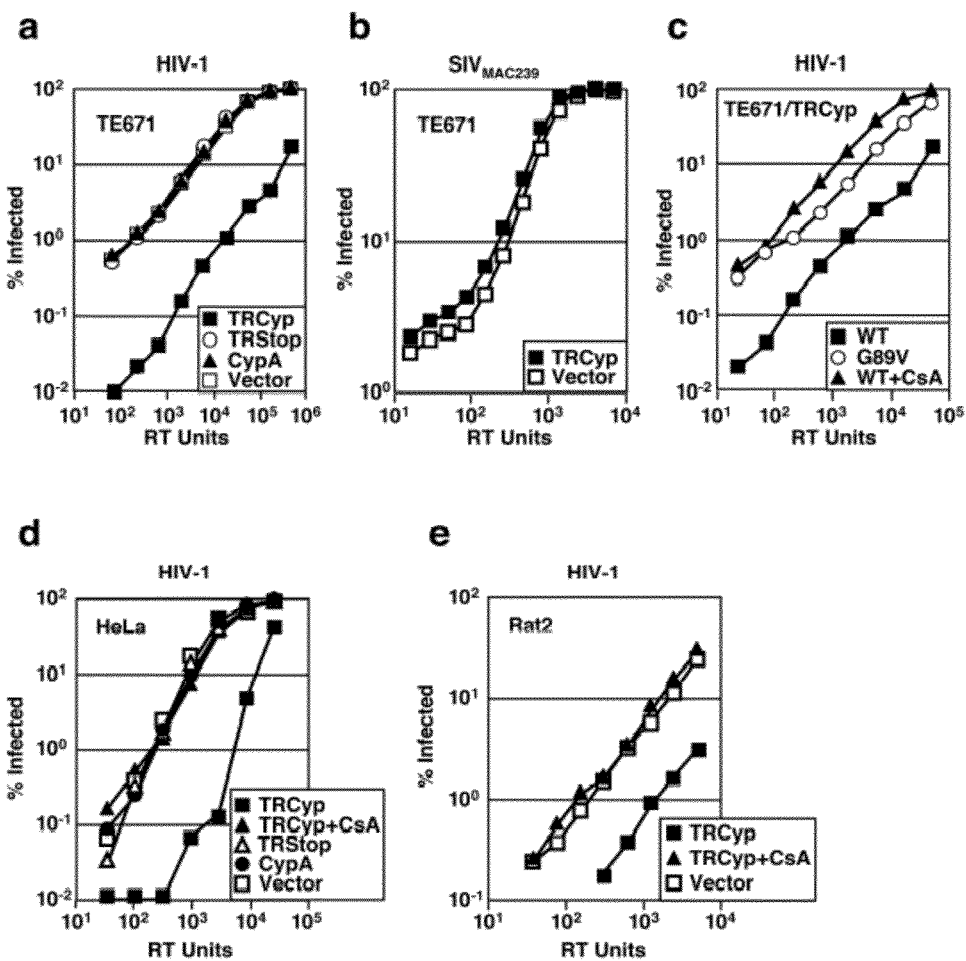
FIGS. 3a-3e. HIV-1 is restricted in human or rat cells transduced with TRIMCyp. TE671 cells transduced with the indicated cDNAs were infected with HIV-1 (a) or $SIV_{MAC239}$ (b). c, TRIMCyp-transduced TE671 cells were infected with HIV-1±CsA or with HIV-1 bearing the capsid G89V mutation. WT, wild type. HeLa cells (d) or Rat2 cells (e) transduced with the indicated cDNAs were infected with HIV-1. Results shown are typical of those obtained in three independent experiments.
Figure 5:
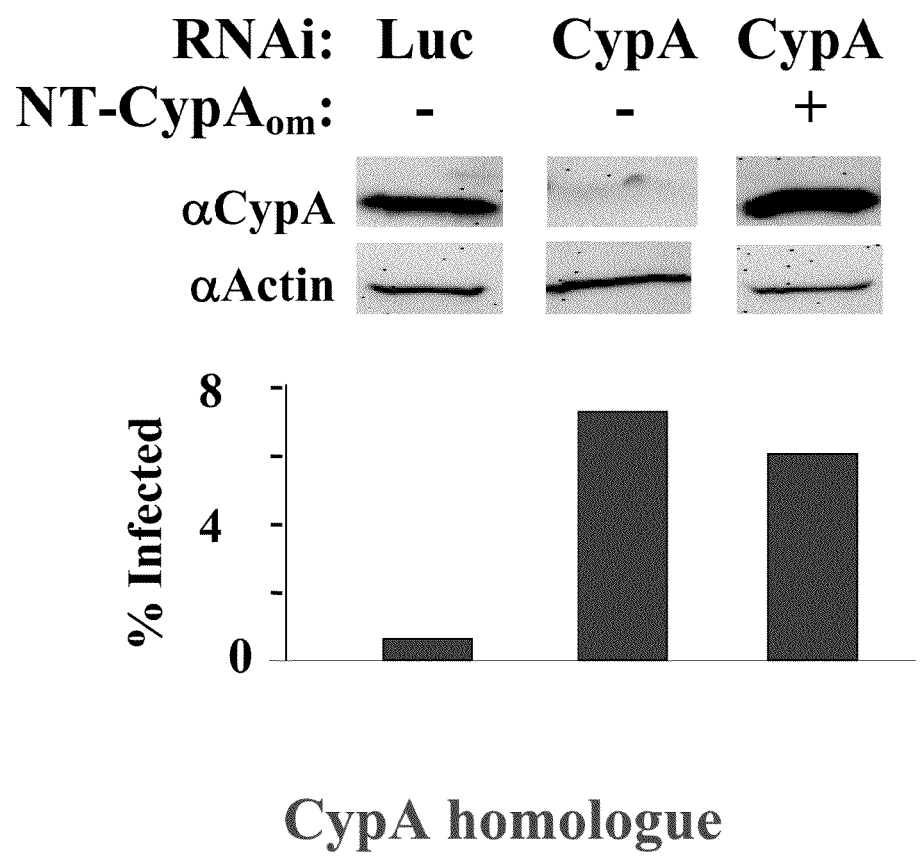
FIG. 5. CypA does not restore restriction in CypA deleted cells. Owl monkey cells were treated with shRNA that knocks down cyclophilin A expression, rescuing HIV-1 from restriction. Cyclophilin A protein was then added back to these cells but failed to restore the HIV-1 restriction. This result showed that the RNAi was targeting a protein other than cyclophilin A, which was necessary for HIV-1 restriction, and led to the cloning of TRIMCyp.

To see if transfer of TRIMCyp confers post-entry restriction of HIV-1 to cells derived from other species, we generated stable human TE671 cell lines expressing TRIMCyp, CypA$_{OM}$, or TRIMStop, a construct in which TRIMCyp has been truncated with a stop codon replacing the first codon of the CypA domain. TE671 cells expressing TRIMCyp were highly resistant to HIV-1 infection, while expression of TRIMStop or CypA$_{OM}$ had no effect on HIV-1 titre (FIG. 3a). As expected, SIV$_{MAC239}$ infection of TE671 cells was unaffected by TRIMCyp (FIG. 3b). HIV-1 restriction mediated by TRIMCyp was bypassed by treating target cells with CsA during infection, or by infection with HIV-1 bearing the G89V capsid mutation that prevents CypA binding (FIG. 3c). HeLa cells transduced with pMIG-TRIMCyp exhibited the same restriction (FIG. 3d). These data demonstrate that HIV-1 restriction by TRIMCyp is capsid-specific and cell-type independent. The CypA domain of TRIMCyp is essential for restriction and disruption of CypA-capsid binding abrogates TRIMCyp-mediated restriction.

Sequencing of OMK genomic DNA, and comparison with human sequence, revealed a complete CypA cDNA between TRIM5 exons 7 and 8 (FIG. 4a). We did not detect an owl monkey TRIM5 allele lacking the CypA insertion. The inserted CypA cDNA is 95% identical to the bona fide owl monkey CypA cDNA, but only 88% identical to human or rhesus macaque CypA, suggesting that CypA insertion into TRIM5 occurred after the divergence of New and Old World primates. Because other New World monkeys lack post-entry HIV-1 restriction activity (1), the CypA insertion appears to be unique to owl monkeys.

The CypA insertion bears the hallmarks of LINE-1 (L1)-mediated retrotransposition (12). These include flanking 16-bp direct repeats consistent with target site duplication, a processed cDNA devoid of introns and accompanied by a poly-A tail, and insertion at a consensus, A-rich L1 endonuclease recognition site (13) (FIG. 4b, c). Mammalian genomes possess many reverse-transcribed CypA pseudogenes which, by definition, are defective (14). TRIMCyp is unusual in that a complete, processed CypA cDNA has generated a new CypA exon that is expressed and spliced to TRIM5 exon 7 to encode a novel chimaeric protein.

TRIMCyp's mechanism of action may be hinted at by its structure and by recent experiments with TRIM5 homologues from other species. The TRIM5 ring-finger domain confers E3 ubiquitin ligase activity (15), suggesting that TRIMCyp attaches ubiquitin to incoming HIV-1 virion proteins. Human cells possess a TRIM5 homologue and HIV-1 infection of these cells is stimulated by proteasome inhibitors (16). We were unable to detect an effect of these drugs on HIV-1 restriction of OMK cells, although these cells are resistant to other drugs, including antibiotics commonly used for selection of mammalian clones. TRIM5 possesses a coiled-coil domain which causes the protein to aggregate and form cytoplasmic bodies (15, 17). TRIMCyp forms similar structures and associates with human TRIM5-α in the yeast two-hybrid system. Though TRIMCyp is functional in non-primate cells (rat fibroblasts, FIG. 3e), restriction may require recruitment of other TRIM family members.

The TRIMCyp carboxy terminus, which is required for restriction (FIG. 3a, d), bears a complete CypA protein that probably functions autonomously to recognize HIV-1 capsid (6). This would not be surprising because cyclophilins frequently exist as discrete domains within complex proteins (18). In rhesus macaques, TRIM5-α accounts for a potent HIV-1 restriction, and the C-terminal B30.2 (SPRY) domain that distinguishes the α-isoform of TRIM5 is essential for this activity (5). RT-PCR with primers based on the owl monkey genomic sequence failed to detect an owl monkey TRIM5-α transcript (one containing the exon 8-encoded B30.2 domain instead of the CypA domain) (FIG. 2c). Because the CypA domain of TRIMCyp substitutes for the B30.2 domain present in macaque TRIM5-α, it is likely that the C terminus of TRIM5-α is also responsible for recognition of incoming viral capsids.

Since the discovery of transposons over 50 years ago (19), it has become clear that these elements play a fundamental role in evolution. L1 elements are the most abundant autonomous retrotransposons in the human genome and are believed to function in trans to retrotranspose Alu elements and processed pseudogenes (20-22). Consistent with the exon shuffling model (23), L1 elements have been shown experimentally to transfer non-L1 sequences into existing genes to generate new gene chimaeras (24). Outside the laboratory, a retrotransposed SVA element forms the last exon of a leptin receptor (25) and one ATM exon retrotransposed into a new genomic location (26). The only previous report of a retrotransposed complete mRNA generating a new exon in a previously existing gene is jingwei in Drosophila melanogaster (27). TRIMCyp is the first example of the genesis of such a chimaeric gene in vertebrates. Interestingly, among primates, owl monkeys have relatively high rates of Alu amplification (28), an indication of increased L1-mediated transposition in these animals. The generation of TRIMCyp probably represents one example of a process that has played a role in the evolution of many genes.

Methods

Plasmids

Most constructs were previously described (4). CSRW, an HIV-1 vector derived from CSGW, bears DsRed (Clontech). p8.9NΔSB is an HIV-1 packaging vector based on pCMVΔR8.91. pMACS-KK.II (Miltenyi Biotec) encodes truncated murine cell-surface major histocompatibility complex (MHC) I H-2K$^K$.

Oligonucleotides encoding shRNAs targeting CypA (Table 1, oligos 9-20) or firefly luciferase (oligos 21 and 22) were ligated into pSUPER (29). The shRNA expression cassette was subcloned into pMSCVΔU3 (30) to generate pMH.

ntTRIMCyp was generated by PCR using oligos 24 and 25, and 23 and 26. TRIMStop replaces the CypA start codon with a stop codon (oligos 25 and 29). ntCypA$_{OM}$ and ntCypA$_H$, are CypA cDNAs resistant to pMH-CypA147 that were generated by PCR using oligos 23-27. ntTRIMCyp, TRIMStop and ntCypA were cloned into pcDNA3.1, pMIG and pLPCX.

Northern Blots

Total cytoplasmic RNA (RNeasy, Qiagen) was fractionated by standard protocols using formaldehyde agarose gel electrophoresis, transferred to Hybond-N+ nylon membranes (Amersham), and fixed by ultraviolet crosslinking (Stratalinker, Stratagene). Probes were owl monkey CypA or human CypB coding sequence, $^{32}$P-labelled by random priming (RediPrimeII, Amersham). Blots were hybridized in Rapid-hyb (Amersham), and visualized on a PhosphorImager (Molecular Devices).

RT-PCR and Real Time RT-PCR

Total RNA from cultured cells or PBMC (RNeasy, Qiagen) was reverse-transcribed into cDNA by random priming (Superscript II, Invitrogen). Primers 1 and 2 were used to amplify TRIMCyp cDNA, primers 5 and 6 to amplify CypA, and primers 30 and 31 to amplify TRIM5-α. Real-time RT-PCR was performed as previously described (30) with product detection using SYBR Green (Molecular Probes). Primers 1 and 2 were used to amplify TRIMCyp. Glyceraldehyde-3-phosphate dehydrogenase (GAPDH) control curves (primers 7 and 8) were identical between samples in the experiments presented here. Cycling conditions were 40 cycles: 94° C., 15 s; 55° C., 15 s; 72° C., 30 s.

cDNA Library Screen

OMK cDNA was size-selected (1,700-2,500 bp) by agarose gel electrophoresis and cloned into pBluescriptII-KS. 100,000 colonies were screened by hybridization with a CypA probe. OMK CypA cDNA was cloned similarly but without size selection.

Genomic PCR

OMK genomic DNA was amplified by PCR using oligos 1 and 2, oligos 3 and 4, or oligos 32 and 33 (Table 1). PCR products were purified (Qiaquick, Qiagen) and sequenced.

Cell Lines and PBMCs

OMK, 293T, TE671, HeLa and Rat2 cells were obtained from ATCC. Owl monkey PBMC were isolated with Ficoll-Paque Plus (Pharmacia), stimulated with 2 µg ml$^{-1}$ PHA (Sigma), and cultured in RPMI supplemented with 20% FBS, 20 U ml$^{-1}$ recombinant human IL-2 (Boehringer Mannheim) and 2 mM L-glutamine.

Drugs

CsA (Bedford Laboratories) was prepared in DMSO at 10 mg ml$^{-1}$. MeIle$^4$-CsA and sanglifehrin (gifts from Novartis, Basel) were prepared in DMSO at 10 mg ml$^{-1}$ and 10 mM, respectively. All drugs were diluted in tissue culture medium to 2.5 µM and added at the time of infection.

Immunoblots

Whole-cell extracts were fractionated by SDS-polyacrylamide gel electrophoresis (PAGE), transferred to PVDF membranes, and probed using rabbit anti-CypA (Biomol), goat anti-TRIM5 (Abcam), or goat anti-actin (Santa Cruz Biotechnology).

Viruses and Retroviral Vectors

Vectors and viruses were produced by transfection of 293T cells using lipofectamine 2000 (Invitrogen) and pseudotyped with VSV-G. pMH, pMIG and pLPCX vectors were produced by co-transfection of the vector plasmid, pCL-Eco and pMD.G using a 5:5:1 ratio of the three plasmids in each transfection. HIV-DsRed and HIV-GFP vectors were produced in 293T cells by co-transfection of CSGW or CSRW with p8.9NΔSB (wild type or G89V mutant) and pMD.G, also at 5:5:1 ratio. HIV/Env-/GFP and SIV/Env-/GFP viruses were produced by cotransfection of the wild type or G89V HIV/Env-/GFP plasmids with pMD.G at a 10:1 ratio. All vectors and viruses were harvested 48 h post-transfection, filtered (0.45-µm filter, Pall Acrodisc), aliquoted, and stored at −80° C. Stocks were normalized by reverse transcriptase activity or p24 ELISA (8).

OMK Cell Transfection and Magnetic Selection

5×10$^5$ OMK cells per well in six-well plates were co-transfected with 1 µg pcDNA3.1 expression vector and 0.1 µg pMACS-K$^K$.II using 6 µl lipofectamine 2000. H-2K$^K$-positive cells were selected (MACSelect KK.II, Miltenyi Biotec) 24 h post-transfection, and either processed for western blot or infected with HIV-GFP.

Generation of Stable Cell Lines

To generate stable RNAi knockdown lines, 1 ml of pMH vector-containing media was pelleted onto OMK cells (1,200 g for 72 min) in 12-well plates. Infection was repeated 24 h later. ntTRIMCyp, TRIMStop and ntCypA$_{OM}$ cDNAs were transduced with either pMIG (OMK and HeLa cells) or pLPCX (TE671 and Rat2 cells). pLPCX-infected cells were selected in 1 μg ml$^{-1}$ puromycin.

Infection Assays

Cells were assayed by flow cytometry 48 to 72 h post-infection to determine the percentage of cells that were GFP-positive (FL-1) or DsRed-positive (FL-2). Cells transduced with pMIG vectors and infected with HIV-DsRed were gated to limit the analysis to GFP-positive cells.

TABLE 1

|    | Oligo Name      | Oligo Sequence                                                                      | SEQ ID NO: |
|----|-----------------|-------------------------------------------------------------------------------------|------------|
| 1  | TRIMCyp781F     | 5'-GTGACTTTGCAGAATCCAAAAACC-3'                                                      | 5          |
| 2  | TRIMCyp963R     | 5'-GGCAATGTCGAAGAACACAGTAGG-3'                                                      | 6          |
| 3  | CypA84 F        | 5'-GGTTCCAAAGACAGCAGAA-3'                                                           | 7          |
| 4  | TRIM1066 R      | 5'-TTCCCTGATGTGATACTTTG-3'                                                          | 8          |
| 5  | CypAStartF      | 5'-ATGGTCAACCCCACCGTGTT-3'                                                          | 9          |
| 6  | CypA147R        | 5'-TCTGTGAAAGCAGGAACCC-3'                                                           | 10         |
| 7  | GAPDHF          | 5'-CCACATCGCTCAGACACCAT-3'                                                          | 11         |
| 8  | GAPDHR          | 5'-GGCAACAATATCCACTTTACCAGAGT-3'                                                    | 12         |
| 9  | sh147sense      | 5'-GATCCCCGGGTTCCTGCTTTCACAGATTCAAGAGATCTGTGAAAGCAGGAACCCTTTTTGGAAA-3'               | 13         |
| 10 | sh147anti       | 5'-AGCTTTTCCAAAAAGGGTTCCTGCTTTCACAGATCTCTTGAATCTGTGAAAGCAGGAACCCGGG-3'               | 14         |
| 11 | sh354sense      | 5'-GATCCCCGACTGAGTGGTTGGATGGCTTCAAGAGAGCCATCCAACCACTCAGTCTTTTTGGAAA-3'               | 15         |
| 12 | sh354anti       | 5'-AGCTTTTCCAAAAAGACTGAGTGGTTGGATGGCTCTCTTGAAGCCATCCAACCACTCAGTCGGG-3'               | 16         |
| 13 | sh375sense      | 5'-GATCCCCGCATGTGGTCTTTGGCAAGGTGTTCAAGAGACACCTTGCCAAAGACCACATGCTTTTTGGAAA-3'         | 17         |
| 14 | sh375anti       | 5'-AGCTTTTCCAAAAAGCATGTGGTCTTTGGCAAGGTGTCTCTTGAACACCTTGCCAAAGACCACATGCGGG-3'         | 18         |
| 15 | sh404sense      | 5'-GATCCCCGCATGAATATTGTGGAGGCCATGGTTCAAGAGACCATGGCCTCCACAATATTCATGCTTTTTGGAAA-3'     | 19         |
| 16 | sh404anti       | 5'-AGCTTTTCCAAAAAGCATGAATATTGTGGAGGCCATGGTCTCTTGAACCATGGCCTCCACAATATTCATGCGGG-3'     | 20         |
| 17 | sh465sense      | 5'-GATCCCCGATCACCATTGCTGACTGTGTTCAAGAGACACAGTCAGCAATGGTGATCTTTTTGGAAA-3'             | 21         |
| 18 | sh465anti       | 5'-AGCTTTTCCAAAAAGATCACCATTGCTGACTGTGTCTCTTGAACACAGTCAGCAATGGTGATCGGG-3'             | 22         |
| 19 | sh3'UTRsense    | 5'-GATCCCCTCTGTGCTCTCGCTGCAGTTTCAAGAGAACTGCAGCGAGAGCACAGATTTTTGGAAA-3'               | 23         |
| 20 | sh3'UTRanti     | 5'-AGCTTTTCCAAAAATCTGTGCTCTCGCTGCAGTTCTCTTGAAACTGCAGCGAGAGCACAGAGGG-3'               | 24         |
| 21 | shLUCsense      | 5'-GATCCCCCGTACGCGGAATACTTCGATTCAAGAGATCGAAGTATTCCGCGTACGTTTTTGGAAA-3'               | 25         |
| 22 | shLUCanti       | 5'-AGCTTTTCCAAAAACGTACGCGGAATACTTCGATCTCTTGAATCGAAGTATTCCGCGTACGGGG-3'               | 26         |
| 23 | CypNTsense      | 5'-TTTGGTTATAAAGGCAGCTGTTTCCATAGGATTATTCCA-3'                                        | 27         |
| 24 | CypNTanti       | 5'-TGGAATAATCCTATGGAAACAGCTGCCTTTATAACCAAA-3'                                        | 28         |
| 25 | CypAStart + Bam | 5'-ACGTGGATCCATGGTCAACCCCACCGTGTT-3'                                                 | 29         |
| 26 | CypAomkStop + R1| 5'-ACGTGAATTCTTATTAGAGTTGTCCACAGTCAGC-3'                                             | 30         |

TABLE 1-continued

| Oligo Name | Oligo Sequence | SEQ ID NO: |
|---|---|---|
| 27 CypAhumStop + R1 | 5'-ACGTGAATTCTTATTCGAGTTGTCCACAGTCAGC-3' | 31 |
| 28 TRIMCypStart + Bam | 5'-ACGTGGATCCGCCATGGCTTCCAGAATCCTGGTC-3' | 32 |
| 29 TrimStop + R1 | 5'-ACGTGAATTCTTATTAGGCTGATGCTACAAGGTCCCA-3' | 33 |

Example 2

Disruption of Human TRIM5α Antiviral Activity by Nonhuman Primate Orthologues

Human immunodeficiency virus type 1 (HIV-1) infection is blocked by the alpha isoform of macaque TRIM5 (TRIM5α$_{rh}$) or by the product of the owl monkey TRIM5-cyclophilin A gene fusion (TRIMCyp). Human TRIM5α potently restricts specific strains of murine leukemia virus (N-MLV) but has only a modest effect on HIV-1. The amino termini of TRIM5 orthologues are highly conserved and possess a coiled-coil domain that promotes homomultimerization. Here we show that heterologous expression of TRIM5α$_{rh}$ or TRIMCyp in human cells interferes with the anti-N-MLV activity of endogenous human TRIM5α (TRIM5α$_{hu}$). Deletion of the cyclophilin domain from TRIMCyp has no effect on heteromultimerization or colocalization with TRIM5α$_{hu}$ but prevents interference with anti-N-MLV activity. These data demonstrate that TRIM5 orthologues form heteromultimers and indicate that C-terminal extensions alter virus recognition by multimers of these proteins.

TRIM5 proteins inhibit the infectivity of a range of different retroviruses in a species-specific fashion (40). The capsid protein (CA) is the viral determinant for susceptibility to this restriction (33, 44). Rhesus macaque TRIM5α (TRIM5α$_{rh}$) restricts human immunodeficiency virus type 1 (HIV-1) replication (5). Human TRIM5α (TRIM5α$_{hu}$) restricts "N-tropic" strains of the murine leukemia virus (N-MLV) (38, 39, 42, 46). In owl monkey cells, HIV-1 is inhibited by TRIMCyp, the product of the TRIM5-cyclophilin (CypA) gene fusion (reference 41, see also Example 1). The restriction activities of TRIM5α$_{rh}$ and TRIMCyp are conferred to nonrestrictive cells upon transduction of the respective cDNAs (reference 5, see also Example 1). CypA modulates the restriction of HIV-1 in human and owl monkey cells in opposite ways: HIV-1 CA binding to the CypA domain of TRIMCyp (34, 35) is necessary for inhibition of HIV-1 in owl monkey cells, while "free" CypA appears to protect HIV-1 from restriction in human cells (4).

At the C-terminus of TRIM5α is a variable SPRY domain that determines the species specificity of restriction (38, 39, 46). In owl monkeys, the SPRY domain was replaced by CypA via L1-mediated retrotransposition (reference 41, see also Example 1). TRIM5α and TRIMCyp both contain a tripartite motif, composed of RING finger, B-Box, and coiled-coil domains (reference 17, see also Example 1), that exhibits E3 ubiquitin ligase activity (5, 36). The coiled-coil domain promotes the formation of TRIM5 homomultimers (17). Here we asked whether TRIM5α or TRIMCyp associates with TRIM5α$_{hu}$ and alters the antiviral activity of the human protein.

We transduced human rhabdomyosarcoma TE671 cells (45) with previously described LPCX vectors (reference 5, see also Example 1) bearing cDNAs for TRIM5α$_{rh}$, TRIMCyp, or owl monkey CypA. Cells were also transduced with a vector expressing TRIMStop, a truncated version of TRIMCyp lacking the CypA domain (see Example 1). Pools of transduced cells were selected in puromycin and then assessed for susceptibility to infection with HIV-1$_{NL-GFP}$ (32). For each transduced population we also tested the effect on HIV-1 infectivity of cyclosporine A (CsA), a drug that competes with HIV-1 CA for binding to CypA (6). We monitored the percentage of infected (GFP-expressing) cells by fluorescence-activated cell sorting (FACS) and the synthesis of viral cDNA in the infected cells using a Southern blot designed to detect full-length, linear viral cDNA and circular viral cDNAs that form in the nucleus (31, 32, 47).

Figure 6:
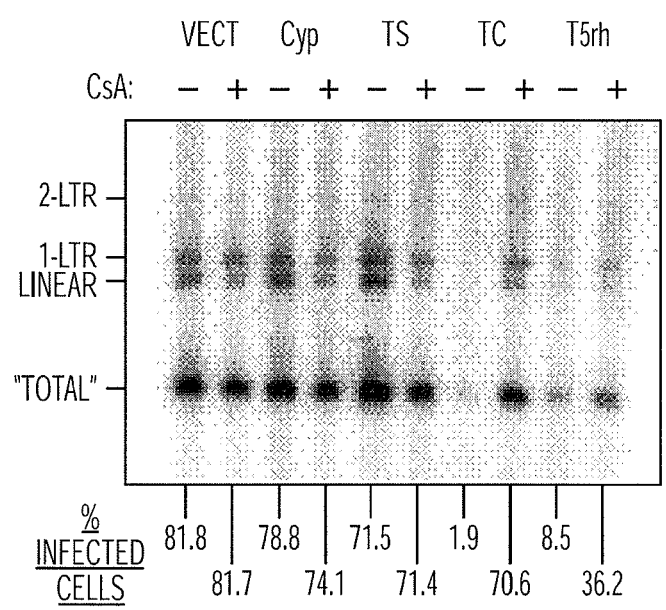
FIG. 6. Inhibition of HIV-1 in human TE671 cells expressing owl monkey TRIMCyp or Rhesus macaque TRIM5α. LPCX-based retroviral vectors were used to transduce the indicated genes into human TE671 cells. Vect, Cyp, TS, TC and T5rh designate, respectively, Vector control, owl monkey CypA, TRIMStop, TRIMCyp, and TRIM5α$_{rh}$. These cells were then infected for 16 h with HIV-1$_{NL\text{-}GFP}$ (pseudotyped vesicular stomatitis virus G protein) in the presence (+) or absence (−) of CsA (5 μM). One twentieth of the cells were maintained in culture for another day and used to determine the percentage of GFP-positive cells by FACS (bottom of the figure). Total DNA was extracted from the remainder of the cells 16 h after infection, and 5 μg of each DNA sample was analyzed by Southern blotting. The positions of the linear, 1-LTR, and 2-LTR HIV-1 cDNA species are indicated on the left. "Total" DNA refers to a band specific to all HIV-1 cDNA forms, including the integrated DNA.

As expected, both TRIM5α$_{rh}$ and TRIMCyp inhibited HIV-1 infection of TE671 cells and inhibited HIV-1 cDNA synthesis (FIG. 6). TRIMCyp inhibited HIV-1 replication roughly fivefold more efficiently than TRIM5α$_{rh}$, consistent with the higher levels of HIV-1 restriction in owl monkey cells than in macaque cells (reference 31, see also Example 1). CsA treatment rescued HIV-1 replication in TRIMCyp-expressing cells (see Example 1). CsA also enhanced HIV-1 infection of TE671-TRIM5α$_{rh}$, indicating that CsA partially countered HIV-1 restriction when TRIM5α$_{rh}$ was expressed in human cells. This result was expected, as CsA also counteracts the restriction to HIV-1 in Old World monkey cells (31). At the high multiplicity of infection used here, CsA had little effect on HIV-1 infectivity; in experiments using a lower multiplicity of infection, CsA modestly decreased HIV-1 infection of control TE671 cells (4).

Next, we analyzed MLV replication in TE671-TRIM5α$_{rh}$, TE671-TRIMCyp, and the control TE671-vector cells. We infected these cells with N- or B-tropic, GFP-expressing MLV vectors (32) that had identical titers in nonrestrictive *Mus dunni* tail fibroblasts and were normalized based on infection of these cells (45). In control cells, B-MLV was ~200-fold more infectious than N-MLV (FIG. 7a). As$_2$O$_3$, a drug that counteracts restriction to N-MLV in TE671 cells (32, 39), specifically increased N-MLV infectivity by 10-fold or more (FIG. 7). In cells expressing TRIM5α$_{rh}$, the N-MLV replication defect was reduced to about 20-fold (FIG. 7a); in cells expressing TRIMCyp, N-tropic restriction was fully abrogated (FIG. 7a). In either case, As$_2$O$_3$ no longer enhanced infectivity, as would be expected for cells lacking the antiviral activity targeting N-MLV.

We also performed the reciprocal experiment, transducing owl monkey OMK cells with TRIM5α$_{hu}$ and challenging them with MLV or HIV-1. TRIM5α$_{hu}$ had only a small (approximately twofold) restrictive effect on the replication of N-MLV and had no effect on B-MLV (FIG. 7b). Restriction of HIV-1 was similar in cells expressing TRIM5α$_{hu}$ to that in the control cells (FIG. 7c), and HIV-1 replication was rescued by CsA in both cell lines, consistent with previous reports (reference 4, see also Example 1). Altogether, the data in FIG. 7 suggest that TRIMCyp is dominant over TRIM5α$_{hu}$.

Figure 8A:
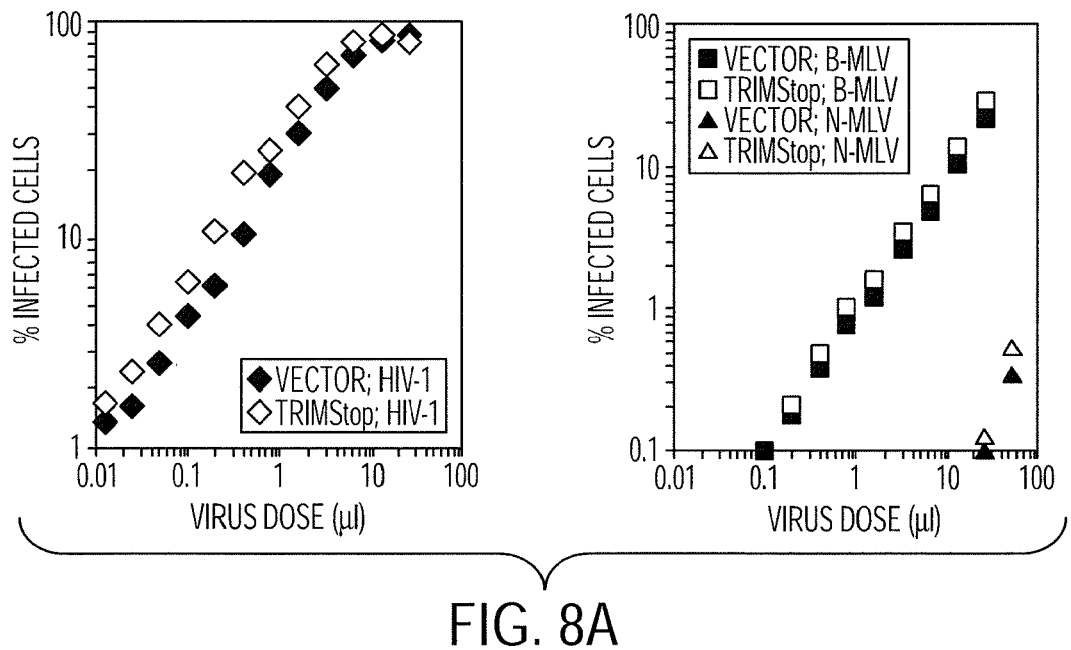
FIGS. 8a-8c. Effect of TRIMStop on TRIM5α$_{hu}$ antiviral activity. (a) TE671-Vector (Vector) cells and TE671-TRIMStop cells were infected with HIV-1$_{NL\text{-}GFP}$ (left panel) or with N- and B-MLV (right panel). Two days later, the percentage of infected (GFP expressing) cells was determined by FACS. (b) Total RNA was prepared from TE671-Vector (Vect), TE671-TRIMCyp (TC), and TE671-TRIMStop (TS), and RT-PCR was used to detect endogenous TRIM5α or TRIMCyp/TRIMStop. RT was performed in the presence (+) or absence (−) of reverse transcriptase. (c) 293T cells were transfected with LPCX (Vect), LPCX-TRIMCyp (TC), or LPCX-TRIMStop (TS), and Western blotting was performed using an antibody specific to TRIM5.
Figure 8B:
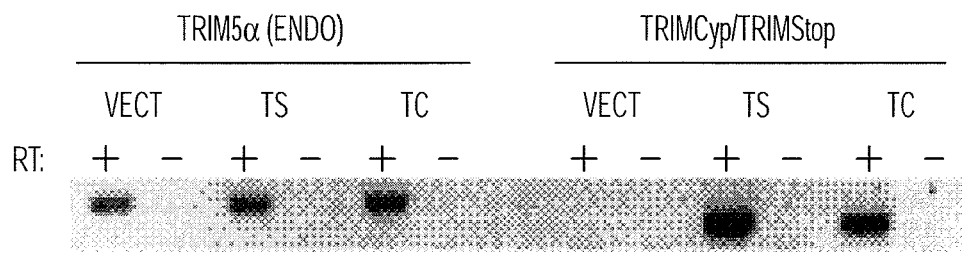
Figure 8C:
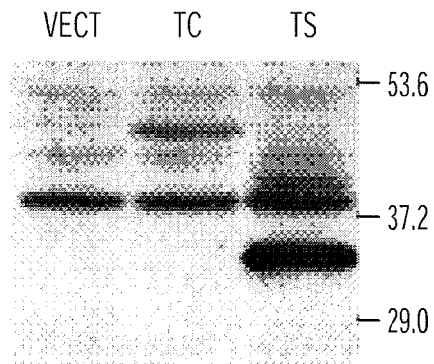

Since TRIMCyp (but not TRIM5α$_{rh}$) completely suppressed the antiviral activity of TRIM5α$_{hu}$, we further investigated the effects of this orthologue. TRIMStop, a truncated version of TRIMCyp lacking the CypA domain (see Example 1), did not affect the capacity of TE671 cells to restrict N-MLV replication (FIG. 8a). To determine if this was because TRIMStop was expressed at lower levels than TRIM-Cyp, we performed reverse transcription-PCR (RT-PCR) using conventional methods (see Example 1). TRIMStop mRNA was expressed at least as well as TRIMCyp mRNA (FIG. 8b); TRIM5α$_{hu}$ was expressed at similar levels in all three cell lines (FIG. 8b). By using Western blotting, we could not detect TRIM5 protein in the TE671 cell lines, but when 293T cells were transfected with the LPCX plasmids, TRIM-Stop was expressed at higher levels than TRIMCyp (FIG. 8c).

Figure 9A:
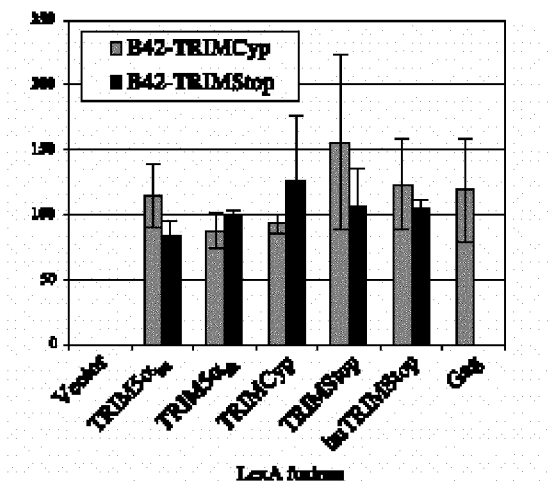
FIGS. 9A-9B. TRIMCyp and TRIMStop both bind TRIM5α$_{hu}$. (A) Yeast two-hybrid system. TRIM5α$_{hu}$, TRIM5α$_{rh}$, TRIMCyp, TRIMStop, huTRIMStop, and HIV-1 Gag were fused to lexA. TRIMCyp and TRIMStop were expressed in fusion with the B42 activation domain. Pairs of fused LexA and B42 expression plasmids were transformed into Saccharomyces cerevisiae strain EGY48. For each transformant, β-galactosidase activity for three colonies is reported in Miller units with the standard deviation. (B) Binding in mammalian cells. TRIM5α$_{hu}$ was fused to GST. 293T cells were transfected with GST or GST-TRIM5α$_{hu}$ (GST-T5α) and cotransfected with LPCX (C), LPCX-TRIMCyp (TC), or LPCXTRIMStop (TS). Thirty-six hours later, the cells were lysed in 50 mM Tris-Cl (pH 8.0), 150 mM NaCl, 1% NP40, 0.1% SDS, and GST was pulled down using glutathione-coated Sepharose beads (Pharmacia). One percent of the pre-pull-down lysate and 25% of the bound proteins were analyzed by Western blotting, using polyclonal antibodies directed against TRIM5, cyclophilin A, or GST.

TRIM5 homomultimerization is promoted by the coiled-coil domain (17), which TRIMCyp also possesses. We hypothesized that the different TRIM5 orthologues heteromultimerize with each other and that TRIMStop did not interfere with TRIM5α$_{hu}$ activity because these particular proteins are incapable of interacting. We used the yeast two-hybrid system to analyze interactions between TRIMStop, TRIM-Cyp, TRIM5α$_{hu}$, TRIM5α$_{rh}$, HIV-1 Gag, and huTRIMStop, a version of TRIM5α$_{hu}$ which, like TRIMCyp, lacks the C-terminal SPRY domain. Fusions of these proteins with LexA and/or B42 were constructed, and the interactions between fusion proteins were analyzed using a previously described system (37) in which reporter gene β-galactosidase activity was assessed with a quantitative assay (43). TRIM-Cyp interacted equally well with TRIMCyp, TRIM5α$_{rh}$, TRIM5α$_{hu}$, TRIMStop, huTRIMStop, and HIV-1 Gag (FIG. 9a). Though TRIMStop was not able to interact with Gag, presumably because the CypA domain was deleted, this protein was as competent as TRIMCyp in interactions with each of the TRIM5 orthologues.

Figure 9B:
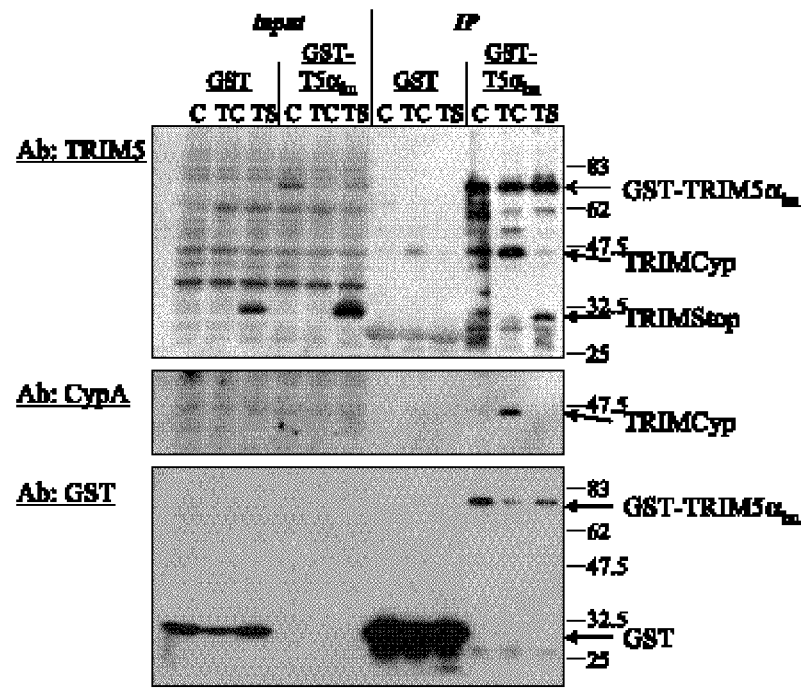

To investigate TRIM5:TRIMCyp heterodimerization in mammalian cells, we expressed TRIM5α$_{hu}$ in fusion with glutathione-S-transferase (GST) and transfected 293T cells with either GST or GST-TRIM5α$_{hu}$. These cells were cotransfected with the LPCX plasmid constructs described above that express TRIMCyp or TRIMStop. GST pull down on glutathione-Sepharose beads (Sigma) followed by Western blotting with anti-TRIM5 antibody showed that both TRIMCyp and TRIMStop associated with TRIM5α$_{hu}$ (FIG. 9b). The blot was also probed with an anti-cyclophilin A antibody, confirming the identity of TRIMCyp (FIG. 9b).

Figure 10:
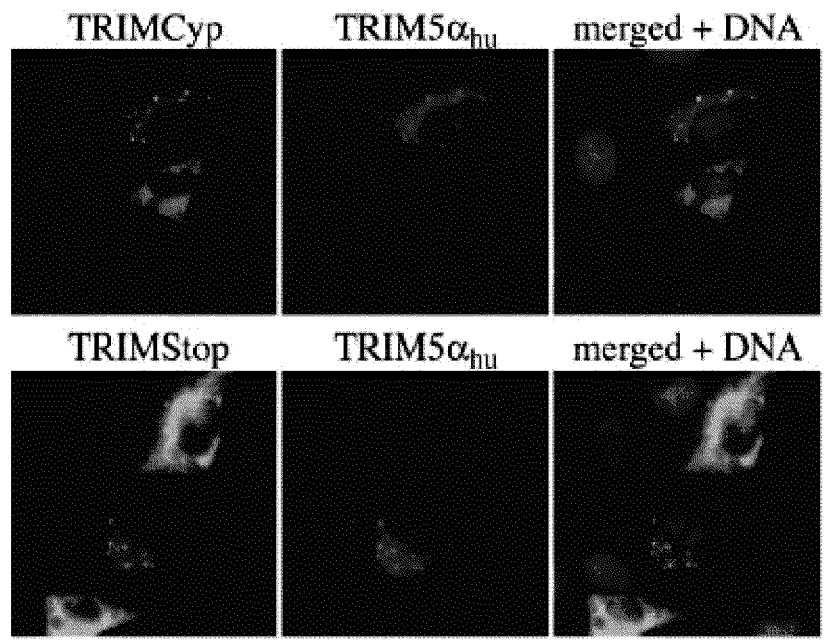
FIG. 10. Colocalization of TRIMCyp and TRIMStop with TRIM5α$_{hu}$. TE671 cells were cotransfected with GST-TRIM5α$_{hu}$ and with 3×FLAG N-terminal-tagged versions of either TRIMCyp or TRIMStop. Thirty-six hours later, cells were fixed with 4% formaldehyde, permeabilized with 0.1% Triton X-100, and probed with antibodies against GST (rabbit polyclonal; Chemicon International) and FLAG (mouse monoclonal; Sigma). Fluorescent staining was done using Alexa488-conjugated goat anti-mouse and Alexa594-conjugated goat anti-rabbit antibodies and Hoechst33342 (all from Molecular Probes) to reveal DNA. Pictures were generated using a Nikon TE300 microscope with the Openlab 3.0 software.

Finally, to examine the distribution of the tagged proteins in cells by immunofluorescence, we cloned TRIMCyp and TRIMStop into p3xFLAG.CMV (SIGMA), encoding N-terminal FLAG-tagged versions of the two proteins. These constructs were each transfected into TE671 cells and detected with anti-FLAG antibody. Both TRIMCyp and TRIMStop were diffusely distributed in the cytoplasm and concentrated around the nucleus in about half of the cells. TRIM5α$_{hu}$, expressed in fusion with GST and detected with anti-GST antibody, was cytoplasmic as well and was partly localized to cytoplasmic bodies as previously reported (17). When TRIM-Cyp or TRIMStop were coexpressed in the same cells with TRIM5α$_{hu}$, both TRIMCyp and TRIMStop showed partial localization to TRIM5α$_{hu}$ cytoplasmic bodies, suggesting that TRIMCyp and TRIMStop are both capable of heterodimerizing with TRIM5α$_{hu}$ in cells. Altogether, the results shown in FIGS. 9 and 10 show that TRIM5 orthologues from different primate species heteromultimerize with each other and that failure of TRIMStop to block restriction activity of TRIM5α$_{hu}$ is not due to failure to multimerize.

In this Example we show that TRIM5 proteins from different primate species interact with each other and can interfere with each other's function. The CypA domain of TRIMCyp is necessary for interference with endogenous TRIM5α (FIG. 9). CsA did not affect interference by TRIMCyp, demonstrating that CypA peptidyl-isomerase activity was not relevant for the effect. A likely possibility is that when TRIM5α$_{hu}$/TRIMCyp heterodimers are formed, the cyclophilin A domain of TRIMCyp interferes with TRIM5α$_{hu}$'s ability to recognize the N-MLV target. Perhaps TRIM5α and TRIM-Cyp function as multimers, with the TRIM5 C-terminus facing the viral target (consistent with the role of CypA in binding HIV-1 CA). Similar to the results reported here with different TRIM5 orthologues, the gamma isoform of macaque TRIM5 was found to inhibit TRIM5α$_{rh}$ anti-HIV restriction activity (5).

Example 3

TRIM5α Selectively Binds a Restriction-Sensitive Retroviral Capsid

In most primate species, retroviral restriction requires the C-terminal SPRY domain unique to the α-isoform of TRIM5, but the mechanism by which susceptible viruses are recognized and targeted for restriction is unknown. Here we show that TRIM5α binds retroviral CA from detergent-stripped virions in a SPRY-dependent manner with sufficient discrimination to account for the exquisite specificity of restriction.

Two independent screens identified TRIM5 as a potent retrovirus restriction element that targets select viruses after entry into primate cells (reference 5, see also Example 1). The biochemical basis for specificity of restriction is only evident in cells of the owl monkey where HIV-1 CA is recognized by the C-terminal cyclophilin domain that is unique to the TRIM5 orthologue found in this genus (reference 41, see also Examples 1 and 2). In all other primates, including humans and macaques, potent CA-specific restriction is conferred by the TRIM5α isoform (5, 38, 39, 42, 46, 48), which possesses a C-terminal SPRY domain (49). The mechanism by which TRIM5α selects retroviruses bearing particular CAs for restriction is unknown, though the TRIM5α SPRY domain is required for restriction and variation in SPRY amino acid residues determines the CA-specificity of given TRIM5α orthologues (48, 50-52).

Conventional biochemical and two-hybrid experiments failed to detect an interaction between TRIM5α and CA. The observation that non-infectious virus-like particles saturate TRIM5α-mediated restriction (53), but only if the particles bear a mature core from a restriction-sensitive virus (2, 4) suggests that the TRIM5α SPRY domain recognizes a complex structure unique to the core of susceptible virions. Consistent with this model, expression within target cells of gag, gag-pol, or gag fragments encoding CA, CA-NC, or ubiquitin-CA-NC fusions, failed to block restriction activity.

Retrovirion cores can be liberated from the viral membrane envelope by detergent (54). HIV-1 virion cores were prepared with several different detergents and mixed with recombinant TRIM5 orthologues. After TRIM5 enrichment by affinity chromatography, CA associated with owl monkey TRIM-CypA, as reported with other methods (reference 41, see also Example 2), but not with the equally potent HIV-1 restriction factor rhesus macaque TRIM5α.

We then selected murine leukemia virus (MLV) for study because, relative to HIV-1, MLV CA remains tightly associated with viral reverse transcription (RT) and preintegration complexes (55, 56). MLV strains bearing an arginine at CA residue 110 (so-called N-MLV) are highly susceptible to restriction by human TRIM5α whereas MLV virions bearing glutamate in this position (B-MLV) are completely resistant to restriction (38, 39, 42, 46).

Figure 11A:
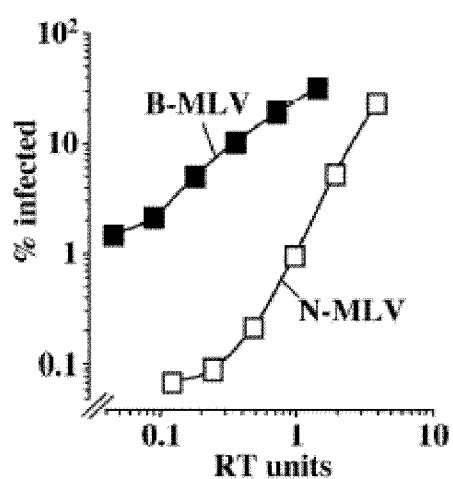
FIGS. 11A-11B. Human TRIM5α binds CA from restricted MLV virions. (A) HeLa cells were infected with VSV G-pseudotyped, N- and B-tropic MLV-GFP vectors after normalization for RT activity and infectivity on nonrestrictive Mus dunni tail fibroblasts. The percentage of infected (GFP-positive) cells was determined by flow cytometry. (B) 293T cells were transfected with plasmids encoding glutathione S-transferase (GST) fusions with full-length TRIM5α or with TRIM5 lacking the SPRY domain. Cells were lysed (50 mM Tris pH 8.0, 150 mM NaCl, 1% NP-40, 0.1% SDS) and mixed for 2 hrs at 4° C. with virions (N-MLV or B-MLV) that had been concentrated by acceleration through 25% sucrose. GST fusions and associated proteins were enriched on glutathione sepharose beads and immunoblotted with goat anti-MLV CA antibody (CA pull-out), or anti-GST antibody (bottom panel). Unbound CA remaining in the binding reaction was probed with anti-MLV CA antibody (CA input). TRIM5 protein domains fused to GST are indicated schematically on the bottom left: RF, ring finger; BB, B box; CC, coiled-coil.
Figure 11B:
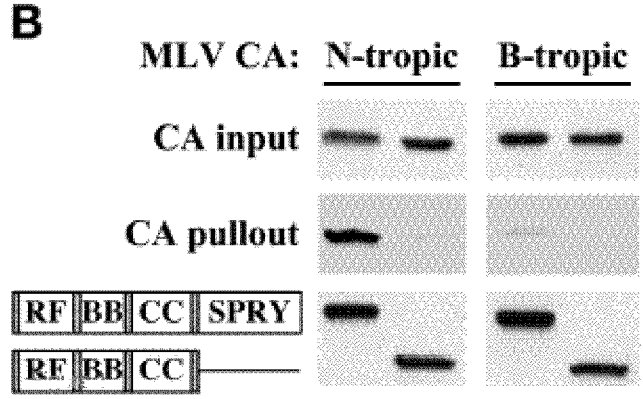

VSV G-pseudotyped N- and B-tropic MLV virions were produced as previously described (45) and, after normalization on non-restrictive *Mus dunni* cells, N-MLV was roughly 100-fold less infectious than B-MLV on HeLa cells (FIG. 11a). Full-length human TRIM5α was then produced as a GST-fusion protein in 293T cells and mixed with purified N-MLV virions. CAp30, the major MLV core protein constituent, associated with TRIM5α (FIG. 11b). CAp30 from B-MLV virions did not associate with TRIM5α (FIG. 11b) demonstrating that TRIM5α binding was specific for restriction sensitive CA. CAp30 did not associate with TRIM5 lacking the SPRY domain (FIG. 11b), indicating that the SPRY-domain is required for CA-recognition.

Retroviral restriction specificity thus seems to be determined by TRIM5α binding to CA in a process that requires the SPRY domain. The fact that TRIM5α recognized retroviral CA presented by detergent-stripped virion cores, but not free CA protein, suggests that the SPRY domain recognizes a complex surface of multimerized CA. Once cores of restriction-sensitive viruses are singled out by the SPRY domain, TRIM5α blocks retroviral RT (5) by a mechanism that awaits elucidation. The invention provides for methods of using the TRIMCyp polypeptides for achieving antiviral activity, wherein the antiviral activity of TRIM5α is harnessed to block HIV-1 infection in people.

Example 4

Human TRIMCyp

Figure 12:
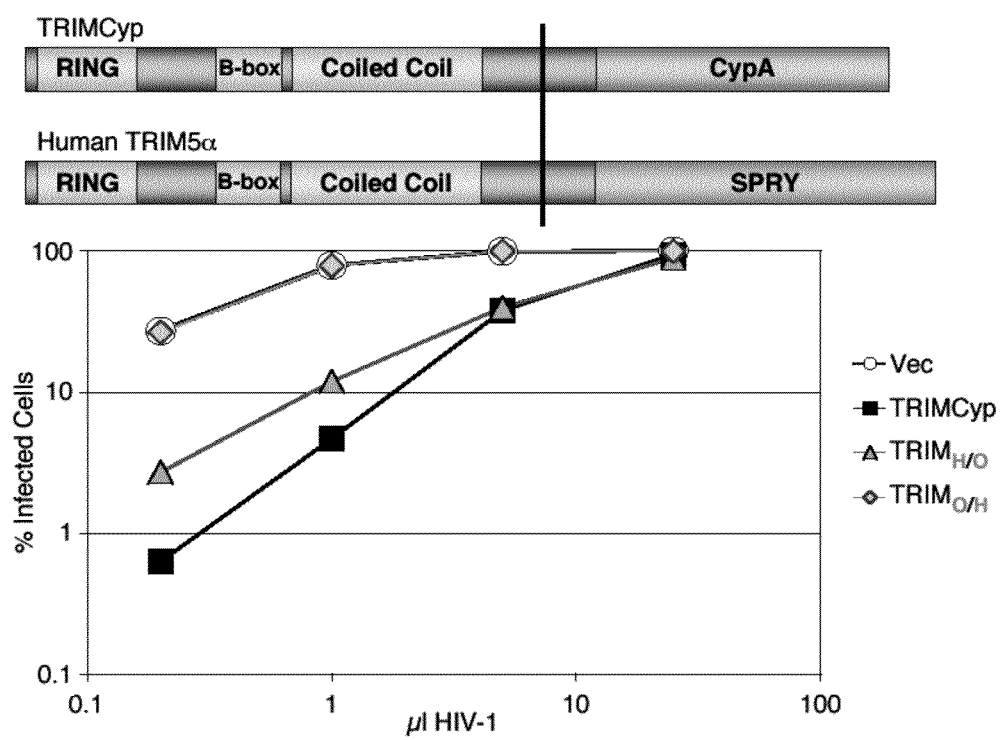
FIG. 12. CypA domain determines TrimCyp specificity. Human TRIM5 is fused to cyclophilin A to make the human equivalent to the owl monkey TRIM Cyp. The human version restricts HIV-1.
Figure 13:
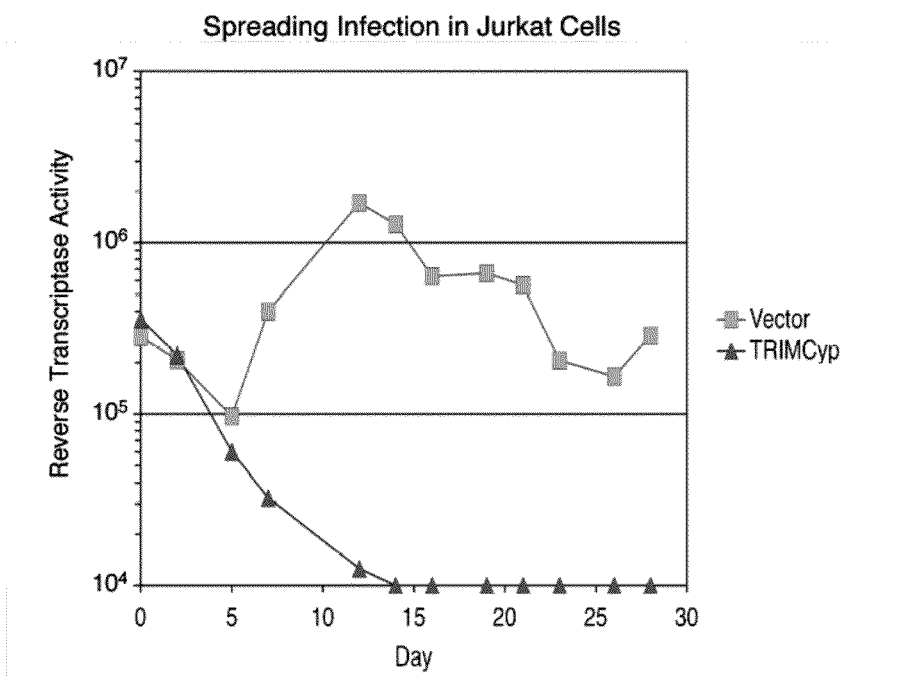
FIG. 13. Human T cells are protected from a spreading, cytopathic HIV-1 infection by TRIMCyp. Retroviral vectors were used to transduce human Jurkat T cells with the cDNA encoding owl monkey TRIMCyp. Control cells were transduced with vector lacking the cDNA. Cells were challenged with full infectious HIV-1 clone NL4-3. Supernatant was collected and assessed for viral reverse transcriptase activity (a quantitative measure of the amount of virus produced in the culture).

Human TRIM5 is fused to cyclophilin A to make the human equivalent to the owl monkey TRIM Cyp (FIG. 12). The human version restricts HIV-1 and is optimized to make the most potent anti-HIV-1 version of human TRIMCyp.

From a gene therapy point of view, the human version is more appealing than the owl monkey version because it would be less likely to be recognized by the human immune system as foreign. Expression of a protein that is not normally expressed in a subject in the subject's cells runs the risk of an immune response against the foreign protein, thereby limiting the effectiveness of the gene therapy. Immune responses include allergic reactions, which could be life-threatening. Alternatively, the cells harboring the foreign gene are eliminated, rendering the therapy useless.

Human hematopoietic stem cells (CD34+ CD38negative) obtained from human placental/umbilical cord blood are transduced using HIV-1-based lentiviral vectors. These cells are then differentiated into T cells and challenged with HIV-1, presenting an effective therapy for blocking HIV-1 infection. Ultimately, human hematopoietic stem cells are mobilized from the bone marrow of HIV-1 infected subjects, the cells are transduced in vitro with lentiviral vectors expressing TRIMCyp, and the cells are injected back into the patient as an auto-transplant.

The following documents are hereby incorporated by reference into this patent application in their entireties for all purposes.

1. Hofmann, W. et al. Species-specific, postentry barriers to primate immunodeficiency virus infection. J. Virol. 73, 10020-10028 (1999).
2. Cowan, S. et al. Cellular inhibitors with Fv1-like activity restrict human and simian immunodeficiency virus tropism. Proc. Natl. Acad. Sci. USA 99, 11914-11919 (2002).
3. Besnier, C., Takeuchi, Y. & Towers, G. Restriction of lentivirus in monkeys. Proc. Natl. Acad. Sci. USA 99, 11920-11925 (2002).
4. Towers, G. J. et al. Cyclophilin A modulates the sensitivity of HIV-1 to host restriction factors. Nature Med. 9, 1138-1143 (2003).
5. Stremlau, M. et al. The cytoplasmic body component TRIM5a restricts HIV-1 infection in Old World monkeys. Nature 427, 848-853 (2004).
6. Luban, J., Bossolt, K. L., Franke, E. K., Kalpana, G. V. & Goff, S. P. Human immunodeficiency virus type 1 Gag protein binds to cyclophilins A and B. Cell 73, 1067-1078 (1993).
7. Braaten, D. & Luban, J. Cyclophilin A regulates HIV-1 infectivity, as demonstrated by gene targeting in human T cells. EMBO J. 20, 1300-1309 (2001).
8. Franke, E. K., Yuan, H. E. & Luban, J. Specific incorporation of cyclophilin A into HIV-1 virions. Nature 372, 359-362 (1994).
9. Thali, M. et al. Functional association of cyclophilin A with HIV-1 virions. Nature 372, 363-365 (1994).
10. Fehr, T., Kallen, J., Oberer, L., Sanglier, J. J. & Schilling, W. Sanglifehrins A, B, C and D, novel cyclophilin-binding compounds isolated from *Streptomyces* sp. A92-308110. II. Structure elucidation, stereochemistry and physico-chemical properties. J. Antibiot. (Tokyo) 52, 474-479 (1999).
11. Jackson, A. L. et al. Expression profiling reveals off-target gene regulation by RNAi. Nature Biotechnol. 21, 635-637 (2003).
12. Kazazian, H. H. Jr. Mobile elements: drivers of genome evolution. Science 303, 1626-1632 (2004).
13. Feng, Q., Moran, J. V., Kazazian, H. H. Jr & Boeke, J. D. Human L1 retrotransposon encodes a conserved endonuclease required for retrotransposition. Cell 87, 905-916 (1996).
14. Zhang, Z., Harrison, P. M., Liu, Y. & Gerstein, M. Millions of years of evolution preserved: a comprehensive catalog of the processed pseudogenes in the human genome. Genome Res. 13, 2541-2558 (2003).
15. Xu, L. et al. BTBD1 and BTBD2 colocalize to cytoplasmic bodies with the RBCC/tripartite motif protein, TRIM5d. Exp. Cell Res. 288, 84-93 (2003).
16. Schwartz, O., Marechal, V., Friguet, B., Arenzana-Seisdedos, F. & Heard, J. M. Antiviral activity of the proteasome on incoming human immunodeficiency virus type 1. J. Virol. 72, 3845-3850 (1998).
17. Reymond, A. et al. The tripartite motif family identifies cell compartments. EMBO J. 20, 2140-2151 (2001).
18. Wu, J., Matunis, M. J., Kraemer, D., Blobel, G. & Coutavas, E. Nup358, a cytoplasmically exposed nucleoporin with peptide repeats, Ran-GTP binding sites, zinc fingers, a cyclophilin A homologous domain, and a leucine-rich region. J. Biol. Chem. 270, 14209-14213 (1995).
19. McClintock, B. The origin and behavior of mutable loci in maize. Proc. Natl. Acad. Sci. USA 36, 344-355 (1950).
20. Esnault, C., Maestre, J. & Heidmann, T. Human LINE retrotransposons generate processed pseudogenes. Nature Genet. 24, 363-367 (2000).
21. Wei, W. et al. Human L1 retrotransposition: cis preference versus trans complementation. Mol. Cell. Biol. 21, 1429-1439 (2001).

22. Dewannieux, M., Esnault, C. & Heidmann, T. LINE-mediated retrotransposition of marked Alu sequences. Nature Genet. 35, 41-48 (2003).
23. Gilbert, W. Why genes in pieces? Nature 271, 501 (1978).
24. Moran, J. V., DeBerardinis, R. J. & Kazazian, H. H. Jr. Exon shuffling by L1 retrotransposition. Science 283, 1530-1534 (1999).
25. Damert, A., Lower, J. & Lower, R. Leptin receptor isoform 219.1: an example of protein evolution by LINE-1-mediated human-specific retrotransposition of a coding SVA element. Mol. Biol. Evol. 21, 647-651 (2004).
26. Ejima, Y. & Yang, L. Trans mobilization of genomic DNA as a mechanism for retrotransposon-mediated exon shuffling. Hum. Mol. Genet. 12, 1321-1328 (2003).
27. Long, M. & Langley, C. H. Natural selection and the origin of jingwei, a chimeric processed functional gene in *Drosophila*. Science 260, 91-95 (1993).
28. Roy-Engel, A. M. et al. Non-traditional Alu evolution and primate genomic diversity. J. Mol. Biol. 316, 1033-1040 (2002).
29. Brummelkamp, T. R., Bernards, R. & Agami, R. A system for stable expression of short interfering RNAs in mammalian cells. Science 296, 550-553 (2002).
30. Asmal, M. et al. Production of ribosome components in effector CD4+ T cells is accelerated by TCR stimulation and coordinated by ERK-MAPK Immunity 19, 535-548 (2003).
31. Berthoux, L., S. Sebastian, E. Sokolskaja, and J. Luban. Lv1 inhibition of human immunodeficiency virus type 1 is counteracted by factors that stimulate synthesis or nuclear translocation of viral cDNA. J. Virol. 78: 11739-11750 (2004).
32. Berthoux, L., G. J. Towers, C. Gurer, P. Salomoni, P. P. Pandolfi, and J. Luban. $As_2O_3$ enhances retroviral reverse transcription and counteracts Ref1 antiviral activity. J. Virol. 77:3167-3180 (2003).
33. Bieniasz, P. D. Restriction factors: a defense against retroviral infection. Trends Microbiol. 11:286-291 (2003).
34. Braaten, D., C. Aberham, E. K. Franke, L. Yin, W. Phares, and J. Luban. Cyclosporine A-resistant human immunodeficiency virus type 1 mutants demonstrate that Gag encodes the functional target of cyclophilin A. J. Virol. 70:5170-5176 (1996).
35. Colgan, J., H. E. Yuan, E. K. Franke, and J. Luban. Binding of the human immunodeficiency virus type 1 Gag polyprotein to cyclophilin A is mediated by the central region of capsid and requires Gag dimerization. J. Virol. 70:4299-4310 (1996).
36. Freemont, P. S. RING for destruction? Curr. Biol. 10:R84-R87 (2000).
37. Gyuris, J., E. Golemis, H. Chertkov, and R. Brent. Cdi1, a human G1 and S phase protein phosphatase that associates with Cdk2. Cell 75:791-803 (1993).
38. Hatziioannou, T., D. Perez-Caballero, A. Yang, S. Cowan, and P. D. Bieniasz. Retrovirus resistance factors Ref1 and Lv1 are species-specific variants of TRIM5_. Proc. Natl. Acad. Sci. USA 101:10774-10779 (2004).
39. Keckesova, Z., L. M. Ylinen, and G. J. Towers. The human and African green monkey TRIM5α genes encode Ref1 and Lv1 retroviral restriction factor activities. Proc. Natl. Acad. Sci. USA 101:10780-10785 (2004).
40. Lee, K., and V. N. KewalRamani. In defense of the cell: TRIM5α interception of mammalian retroviruses. Proc. Natl. Acad. Sci. USA 101: 10496-10497 (2004).
41. Nisole, S., C. Lynch, J. P. Stoye, and M. W. Yap. A Trim5-cyclophilin A fusion protein found in owl monkey kidney cells can restrict HIV-1. Proc. Natl. Acad. Sci. USA 101:13324-13328 (2004).
42. Perron, M. J., M. Stremlau, B. Song, W. Ulm, R. C. Mulligan, and J. Sodroski. TRIM5α mediates the postentry block to N-tropic murine leukemia viruses in human cells. Proc. Natl. Acad. Sci. USA 101:11827-11832 (2004).
43. Stern, M., R. Jensen, and I. Herskowitz. Five SWI genes are required for expression of the HO gene in yeast. J. Mol. Biol. 178:853-868 (1984).
44. Stoye, J. P. An intracellular block to primate lentivirus replication. Proc. Natl. Acad. Sci. USA 99:11549-11551 (2002).
45. Towers, G., M. Bock, S. Martin, Y. Takeuchi, J. P. Stoye, and O. Danos. A conserved mechanism of retrovirus restriction in mammals. Proc. Natl. Acad. Sci. USA 97:12295-12299 (2000).
46. Yap, M. W., S, Nisole, C. Lynch, and J. P. Stoye. TRIM5α protein restricts both HIV-1 and murine leukemia virus. Proc. Natl. Acad. Sci. USA 101:10786-10791 (2004).
47. Zennou, V., C. Petit, D. Guetard, U. Nerhbass, L. Montagnier, and P. Charneau. HIV-1 genome nuclear import is mediated by a central DNA flap. Cell 101:173-185 (2000).
48. Song B, Javanbakht H, Perron M, Park do H, Stremlau M, Sodroski J. Retrovirus restriction by TRIM5alpha variants from old world and new world primates. *J Virol* 79:3930-3937 (2005).
49. Ponting C, Schultz J, Bork P. SPRY domains in ryanodine receptors (Ca(2+)-release channels). Trends Biochem Sci 22:193-194 (1997).
50. Yap M W, Nisole S, Stoye J P. A single amino acid change in the SPRY domain of human Trim5alpha leads to HIV-1 restriction. Curr Biol 15:73-78 (2005).
51. Sawyer S L, Wu L I, Emerman M, Malik H S. Positive selection of primate TRIM5alpha identifies a critical species-specific retroviral restriction domain. Proc Natl Acad Sci USA 102:2832-2837 (2005).
52. Stremlau M, Perron M, Welikala S, Sodroski J. Species-Specific Variation in the B30.2(SPRY) Domain of TRIM5 {alpha} Determines the Potency of Human Immunodeficiency Virus Restriction. *J Virol* 79:3139-3145 (2005).
53. Towers G, Collins M, Takeuchi Y. Abrogation of Ref1 retrovirus restriction in human cells. J Virol 76:2548-2550 (2002).
54. Welker R, Hohenberg H, Tessmer U, Huckhagel C, Krausslich H G. Biochemical and structural analysis of isolated mature cores of human immunodeficiency virus type 1. J Virol 74:1168-1177 (2000).
55. Bowerman B, Brown P O, Bishop J M, Varmus H E. A nucleoprotein complex mediates the integration of retroviral DNA. Genes Dev 3:469-478 (1989).
56. Fassati A, Goff S P. Characterization of intracellular reverse transcription complexes of Moloney murine leukemia virus. J Virol 73:8919-8925 (1999).

TRIMCyp and CypA sequences have been deposited in GenBank (accession numbers AY646198 (SEQ ID NO: 1), AY646199 (SEQ ID NO: 2) and AY646200 (SEQ ID NO: 3)).

As various changes can be made in the above methods and compositions without departing from the scope and spirit of the invention as described, it is intended that all subject matter contained in the above description, shown in the accompanying drawings, or defined in the appended claims be interpreted as illustrative, and not in a limiting sense.

What is claimed is:

1. An isolated polypeptide comprising the amino acid sequence of SEQ ID NO:4.

2. An isolated polypeptide consisting essentially of the amino acid sequence of SEQ ID NO:4.

3. An isolated polypeptide comprising an amino acid sequence at least about 85% identical to SEQ ID NO: 4.

4. The isolated polypeptide of claim 3, wherein the polypeptide comprises an amino acid sequence at least about 90% identical to SEQ ID NO: 4.

5. The isolated nucleic acid of claim 3, wherein the polypeptide comprises an amino acid sequence at least about 95% identical to SEQ ID NO: 4.

6. An isolated cell comprising the polypeptide of claim 1, 2, 3, 4 or 5.

7. An isolated stem cell comprising the polypeptide of claim 1, 2, 3, 4 or 5.

8. A method for inhibiting HIV-1 in a subject, comprising administering to the subject an isolated TRIM-cyclophilin polypeptide of claim 1 or 2.

9. A composition comprising the polypeptide of claim 1, 2, 3, 4 or 5.

10. The composition of claim 9, wherein the carrier comprises a liposome.

* * * * *